United States Patent [19]

Norbeck et al.

[11] Patent Number: 4,988,703
[45] Date of Patent: Jan. 29, 1991

[54] CARBOCYCLIC NUCLEOSIDE ANALOGS WITH ANTIVIRAL ACTIVITY

[75] Inventors: Daniel W. Norbeck, Lindenhurst, Ill.; Terry J. Rosen, East Lyme, Conn.; Hing L. Sham, Gurnee, Ill.

[73] Assignee: Abbott Laboratories, Abbott Park, Ill.

[21] Appl. No.: 355,594

[22] Filed: May 22, 1989

[51] Int. Cl.$^5$ .............. A61K 31/52; C07D 473/18; C07D 473/30; C07D 473/34
[52] U.S. Cl. .................. 514/262; 514/81; 514/86; 514/261; 514/263; 514/265; 514/266; 514/274; 544/243; 544/244; 544/265; 544/267; 544/272; 544/276; 544/277; 544/311; 544/312; 544/313; 544/314; 544/317; 544/322; 544/329; 562/13; 564/1; 564/46
[58] Field of Search .............. 544/244, 265, 267, 272, 544/277, 276; 514/81, 261, 263, 265, 266, 262

[56] References Cited

U.S. PATENT DOCUMENTS

| | | | |
|---|---|---|---|
| 3,923,792 | 12/1975 | Albrecht et al. | 544/317 |
| 4,016,267 | 4/1977 | Albrecht et al. | 514/157 |
| 4,548,818 | 10/1985 | Kjellin et al. | 514/263 |
| 4,617,304 | 10/1986 | Ashton et al. | 514/261 |
| 4,644,001 | 2/1987 | Kjellin et al. | 514/263 |
| 4,782,062 | 11/1988 | Tolman et al. | 514/262 |
| 4,855,466 | 8/1989 | Zahler et al. | 549/546 |

FOREIGN PATENT DOCUMENTS 0291917 11/1988 European Pat. Off. .

OTHER PUBLICATIONS

Temple, J. Med. Chem. 5, 866 (1962).
Marquez, Medicinal Research Reviews, 6, 1–40 (1986).
Engel-Masoliver, et al., Chemical Abstracts, vol. 107: 236375e (1987).

Primary Examiner—Diana Rivers
Attorney, Agent, or Firm—Steven R. Crowley

[57] ABSTRACT

An antiviral compound of the formula:

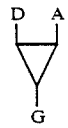

wherein A is selected from a purin-9-yl group, a heterocyclic isostere of a purin-9-yl group, a pyrimidin-1-yl group and a heterocyclic isostere of a pyrimidin-1-yl group; and
G and D are independently selected from hydrogen, $C_1$ to $C_{10}$ alkyl and substituted derivatives thereof, —OH, —C(O)H, —CO$_2$R$_1$ *wherein* $R_1$ is hydrogen or $C_1$ to $C_{10}$ alkyl and —OCH$_2$PO$_3$H$_2$, with the proviso that one of D or G is other than hydrogen or $C_1$ to $C_{10}$ alkyl; or a pharmaceutically acceptable salt thereof.

5 Claims, No Drawings

CARBOCYCLIC NUCLEOSIDE ANALOGS WITH ANTIVIRAL ACTIVITY

TECHNICAL FIELD

The present invention relates to novel compounds and compositions which have antiviral activity, processes for making such compounds, synthetic intermediates employed in these processes and a method for treating a host in need of antiviral treatment.

BACKGROUND ART

Viruses are implicated in a variety of animal and human diseases. Numerous approaches have been proposed to combat these pathogens which include, but are not limited to, herpesviruses 1 and 2 (HSV-1 and HSV-2), influenza viruses A, B and C (orthomyxoviruses), parainfluenza viruses 1–4, mumps virus (paramyxovirus), adenoviruses, respiratory syncytial virus, Epstein-Barr virus, rhinoviruses, human immunodeficiency viruses (HIV), polioviruses, coxsackieviruses, echoviruses, rubella virus, varicella-zoster virus, neurodermotropic virus, variola virus, cytomegalovirus, hepatitis A, B and non-A, non-B viruses, papoviruses and rabies virus.

One approach in the development of antiviral compounds has been to identify compounds which interfere with the normal viral metabolism of nucleosides. Because the structures of these compounds are usually closely related to nucleosides which occur naturally in the mammalian host, few have good activity against the virus without untoward side effects. Some of the few compounds having activity are very expensive to produce. Thus, there is a continuing need for new compounds which act to kill viruses, to inhibit viral replication or to block the pathogenic actions of viruses.

Known antiviral, antibacterial, anticancer and cardiovascular compounds which are closely related to or derivatives of nucleosides include those disclosed in the following references:

Ashton, U.S. Pat. No. 4,617,304, issued Oct. 14, 1986, discloses ((hydroxymethy)cyclopropyl)methyl)-substituted purine and pyrimidine analogs which are useful as antiviral agents.

Albrecht, U.S. Pat. Nos. 4,016,267 and 3,923,792, issued Apr. 5, 1977 and Dec. 2, 1975, respectively, disclose cyclopropyl-, cyclopropylmethyl- and cyclopentyl-substituted nucleoside analogs which are useful as antibacterial agents.

Kjellin, U.S. Pat. Nos. 4,644,001 and 4,548,818, issued Feb. 17, 1987 and Oct. 22, 1985, respectively, disclose cyclopropyl-, cyclobutyl- and cyclopentyl-substituted purine analogs which are useful for treating obstructive airway disease or cardiac disease.

Temple, J. Med. Chem. 5 866 (1962), discloses cyclopropyl-substituted purine analogs which are useful for treating human epidermal carcinoma.

Masoliver, Spanish Patent No. ES519898, published Mar. 16, 1984, discloses cyclopropyl-substituted purine analogs.

Tolman, U.S. Pat. No. 4,782,062, issued Nov. 1, 1988, discloses 9-((Z)-2-(hydroxymethyl)cyclobutylmethyl)-guanine as a viral thymidine kinase inhibitor.

Shimada, European Patent Application No. EP0291917, published Nov. 23, 1988, discloses oxetanocin and oxetanocin analogs.

Marquez, Medicinal Research Reviews, 6 1–40 (1986), discloses substituted-cyclopentyl nucleoside analogs.

None of the above-mentioned references disclose or suggest the compounds of the present invention.

DISCLOSURE OF THE INVENTION

In accordance with the present invention there are antiviral compounds of the formula:

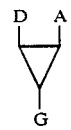

or a pharmaceutically acceptable salt thereof.

A is selected from a purin-9-yl group, a heterocyclic isostere of a purin-9-yl group, a pyrimidin-1-yl group and a heterocyclic isostere of a pyrimidin-1-yl group.

G and D are independently selected from hydrogen, $C_1$ to $C_{10}$ alkyl and substituted derivatives thereof, —OH, —C(O)H, —CO$_2$R$_1$ wherein R$_1$ is hydrogen or $C_1$ to $C_{10}$ alkyl and —OCH$_2$PO$_3$H$_2$, with the proviso that one of D or G is other than hydrogen or $C_1$ to $C_{10}$ alkyl.

Substituted derivatives of $C_1$ to $C_{10}$ alkyl include:

(1) —(CH(R$_{30}$))$_y$CH$_2$OH wherein y is 0 or 1 and R$_{30}$ is hydrogen or —OH, (2) —(CH(R$_{31}$))$_y$CH$_2$OR$_{20}$ wherein y is 0 or 1 and R$_{31}$ is hydrogen or —OR$_{32}$ wherein R$_{20}$ and R$_{32}$ are independently selected from $C_1$ to $C_6$ alkyl and a hydroxy protecting group, (3) —(CH(R$_{33}$))$_y$CH$_2$OC(O)R$_{21}$ wherein y is 0 or 1 and R$_{33}$ is hydrogen or —OC(O)R$_{34}$ wherein R$_{21}$ and R$_{34}$ are independently selected from $C_1$ to $C_{10}$ alkyl, (4) —(CH$_2$)$_y$CH$_2$OC(O)CH(R$_{22}$)(NHR$_{23}$) wherein y is 0 or 1 and R$_{22}$ is the side chain of any of the naturally occurring amino acids and R$_{23}$ is hydrogen or —C(O)CH(R$_{24}$)(NH$_2$) wherein R$_{24}$ is the side chain of any of the naturally occurring amino acids, (5) —(CH$_2$)$_z$R$_{35}$ wherein z is 1 or 2 and R$_{35}$ is —SH, —Cl, —F, —Br, —I, —CN or —N$_3$, (6) —CH$_2$NR$_1$R$_2$ wherein R$_1$ and R$_2$ are independently selected from hydrogen and $C_1$ to $C_{10}$ alkyl, (7) —CH$_2$CH$_2$PO$_3$H$_2$ and (8) —CH$_2$CO$_2$R$_3$ wherein R$_3$ is hydrogen, $C_1$ to $C_{10}$ alkyl, carboxyalkyl or aminoalkyl.

The term "$C_1$ to $C_{10}$ alkyl" as used herein refers to straight or branched chain alkyl radicals containing from 1 to 10 carbon atoms including, but not limited to, methyl, ethyl, isopropyl, n-butyl, isobutyl, sec-butyl, n-pentyl, 1-methylbutyl, 2,3-dimethylbutyl, 2-methylpentyl, 2,2-dimethylpropyl, n-hexyl, n-heptyl, n-octyl, n-nonyl, n-decyl and the like.

The term "haloalkyl" as used herein refers to a $C_1$ to $C_{10}$ alkyl group in which one or more hydrogen atoms are replaced by halogen including, but not limited to, fluoromethyl, chloromethyl, difluoromethyl, trifluoromethyl, 2-chloroethyl, 2-fluoroethyl and the like.

The term "hydroxyalkyl" as used herein refers to a hydroxy group appended to a $C_1$ to $C_{10}$ alkyl radical including, but not limited to, hydroxymethyl, hydroxyethyl and the like.

The term "azidoalkyl" as used herein refers to an azido group (—N$_3$) appended to a $C_1$ to $C_{10}$ alkyl radical including, but not limited to, azidomethyl and the like.

The term "alkenyl" as used herein refers to a straight or branched chain radical containing from 2 to 10 carbon atoms and also containing a carbon-carbon double bond including, but not limited to, vinyl, propenyl and the like.

The term "haloalkenyl" as used herein refers to an alkenyl group in which one or more hydrogen atoms are replaced by halogen including, but not limited to, 2-halovinyl, 3,3,3-trifluoropropenyl and the like.

The term "cyanoalkenyl" as used herein refers to a cyano group (—CN) appended to an alkenyl radical including, but not limited to, 2-cyanoethenyl and the like.

The term "alkoxycarbonylalkenyl" as used herein refers to an alkoxycarbonyl group appended to an alkenyl radical including, but not limited to, 2-(alkoxycarbonyl)ethenyl and the like.

The terms "alkoxy" and "thioalkoxy" as used herein refer to —OR$_{25}$ and —SR$_{25}$, respectively, wherein R$_{25}$ is a C$_1$ to C$_{10}$ alkyl group.

The term "carboxyalkyl" as used herein refers to a carboxylic acid group (—COOH) appended to a C$_1$ to C$_{10}$ alkyl radical.

The term "alkoxycarbonyl" as used herein refers to —C(O)R$_{26}$ wherein R$_{26}$ is an alkoxy group.

The term "aminoalkyl" as used herein refers to an amino group (—NH$_2$) appended to a C$_1$ to C$_{10}$ alkyl radical.

The term "alkynyl" as used herein refers to a C$_2$ to C$_6$ straight or branched carbon chain which contains a carbon-carbon triple bond including, but not limited to, ethynyl, propynyl, butynyl and the like.

The term "halo" or "halogen" as used herein refers to Cl, Br, F or I.

The term "side chain of any of the naturally occurring amino acids" as used herein refers to the functionality appended at the alpha carbon of any of the naturally occurring amino acids and includes, but is not limited to hydrogen (glycine), methyl (alanine), isopropyl (valine), hydroxymethyl (serine), benzyl (phenylalanine), and the like.

The term "N-protecting group" as used herein refers to those groups intended to protect nitrogen atoms against undesirable reactions during synthetic procedures and includes, but is not limited to, acyl, acetyl, pivaloyl, t-butylacetyl, trichloroethoxycarbonyl, t-butoxycarbonyl (Boc), benzyloxycarbonyl (Cbz) or benzoyl groups or other nitrogen protecting groups known to those skilled in organic synthesis such as those disclosed in Greene, "Protective Groups in Organic Synthesis", pp. 218–287, (J. Wiley & Sons, 1981).

The term "hydroxy protecting group" as used herein refers to those groups intended to protect a hydroxy group against undesirable reactions during synthetic procedures and includes, but is not limited to, substituted methyl ethers, for example, methoxymethyl, benzyloxymethyl, 2-methoxyethoxymethyl, 2-(trimethylsilyl)ethoxymethyl and tetrahydropyranyl; substituted ethyl ethers, for example, 2,2,2-trichloroethyl, t-butyl, benzyl and triphenylmethyl; silyl ethers, for example, trimethylsilyl, t-butyldimethylsilyl and t-butyldiphenylsilyl; acyl groups such as acetyl and benzoyl; sulfonates such as mesylate and tosylate; or other hydroxy protecting groups known to those skilled in organic synthesis such as those disclosed in Greene, "Protective Groups in Organic Synthesis", pp. 10–71, (J. Wiley & Sons, 1981).

The term "heterocyclic isostere of a purin-9-yl group" as used herein refers to a heterocyclic group which has a similar structure and similar properties when compared to a purin-9-yl group. In addition, the isostere may contain different atoms and not necessarily the same numbers of atoms as long the isostere possesses the same total or valence electrons in the same arrangement as does a purin-9-yl group. For example, well known isosteric pairs of molecules include the pair carbon monoxide and atmospheric nitrogen and the pair cyanide ion and acetylide ion. Heterocyclic isosteres of a purin-9-yl group include, but are not limited to, compounds of the formula:

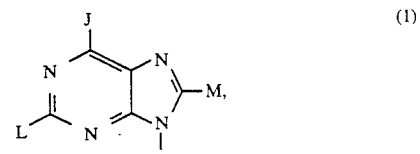

(1)

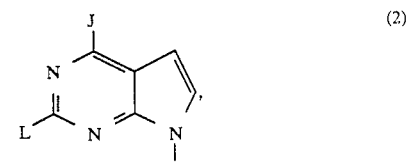

(2)

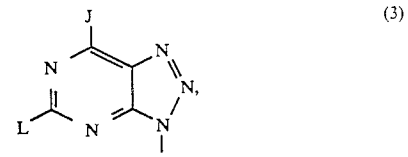

(3)

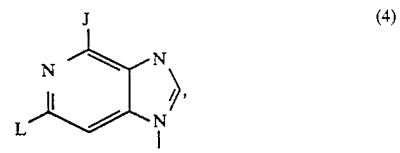

(4)

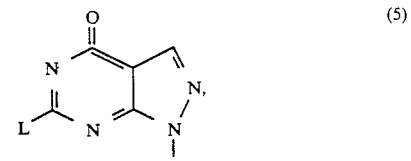

(5)

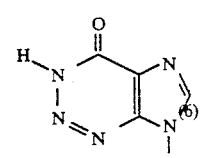

(6)

and

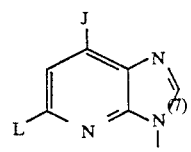

(7)

wherein J and L are independently selected from hydrogen, —OH, halogen, alkoxy, —SH, thioalkoxy, —N₃,

wherein m is 1 to 5, or —NR₁R₂ wherein R₁ and R₂ are independently selected from hydrogen and C₁ to C₁₀ alkyl, —NH-C(O)R₃ wherein R₃ is hydrogen, C₁ to C₁₀ alkyl, carboxyalkyl or aminoalkyl, —N=CHNR₄R₅ wherein R₄ and R₅ are independently selected from C₁ to C₁₀ alkyl, —N(R₆)OR₇ wherein R₆ and R₇ are independently selected from hydrogen and C₁ to C₁₀ alkyl, and —N(R₈)NR₉R₁₀ wherein R₈, R₉ and R₁₀ are independently selected from hydrogen and C₁ to C₁₀ alkyl; and wherein M is C₁ to C₁₀ alkyl, halogen,

wherein m is 1 to 5, or —NR₁R₂ wherein R₁ and R₂ are as defined above.

The term "heterocyclic isostere of a pyrimidin-1-yl group" as used herein refers to a heterocyclic group which has a similar structure and similar properties when compared to a pyrimidin-1-yl group. In addition, the isostere may contain different atoms and not necessarily the same number of atoms as long as the isostere possesses the same total or valence electrons in the same arrangement as does a pyrimidin-1-yl group. For example, well known isosteric pairs of molecules include the pair carbon monoxide and atmospheric nitrogen and the pair cyanide ion and acetylide ion. Heterocyclic isosteres of a pyrimidin-1-yl group include, but are not limited to, compounds of the formula:

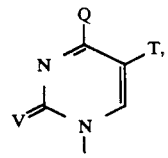 (8)

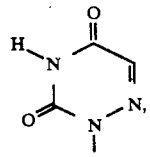 (9)

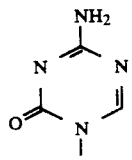 (10)

and

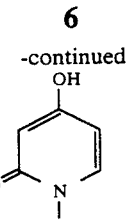 (11)

wherein V is O or S;
Q is —OH, —SH, alkoxy, thioalkoxy, halogen,

wherein m is 1 to 5, or —NR₁R₂ wherein R₁ and R₂ are as defined above, or —NHC(O)R₃ wherein R₃ is as defined above; and T is hydrogen, C₁ to C₁₀ alkyl, haloalkyl, hydroxyalkyl, azidoalkyl, halogen, cyano, nitro, alkenyl, haloalkenyl, cyanoalkenyl, alkoxycarbonylalkenyl, alkynyl, formyl, —NR₁R₂ wherein R₁ and R₂ are as defined above, —NHOH, —SH,

wherein m is 1 to 5, or —CH₂NR₁R₂ wherein R₁ and R₂ are as defined above.

The compounds of the present invention may be prepared by various methods disclosed in Schemes I to IX.

According to one method (Scheme I), the adduct of butadiene and ethyl diazoacetate (the compound of formula 1) is hydrolyzed in basic solution to the acid 2 which is treated with diphenylphosphorylazide in the presence of t-butyl alcohol to form the protected amino derivative (the compound of formula 3). In order to obtain the monohydroxy derivative, I$_A$, the double bond of compound 3 is treated with a hydroborating agent such as borane.THF, followed by oxidation in alkaline solution with an oxidizing agent such as hydrogen peroxide to give the protected amino alcohol 4, which is deprotected in acidic solution to provide I$_A$. In order to obtain the dihydroxy derivative, I$_B$, the double bond of compound 3 is oxidized with an oxidizing agent such as potassium permanganate in basic solution to give the protected amino diol 5, which is deprotected in acidic solution to give I$_B$. As demonstrated in subsequent schemes, compounds of Formula I$_A$ and I$_B$ are key intermediates used in the synthesis of the purines, pyrimidines and their heterocyclic isosteres disclosed in this application.

According to one method (Scheme II), compound 6 is reduced with a reducing agent such as lithium aluminum hydride to the diol 7. The hydroxyl groups are protected with benzoyl groups by treating compound 7 with benzoyl chloride in the presence of an acid acceptor such as pyridine and the double bond oxidized to the hydroxy compound 8 by hydroboration/oxidation as discussed in Scheme I. The hydroxy group of compound 8 is then oxidized to the carboxylic acid with an oxidizing agent such as sodium periodate in the presence of a catalytic amount of a catalyst such as ruthenium trichloride. The carbobenzoxy (CBZ) protected amine 10 is prepared by treatment of compound 9 with diphenylphosphorylazide in the presence of benzyl alcohol. The hydroxyl protecting groups are removed by treatment with a base such as sodium methoxide and the amine protecting group is removed by hydrogenolysis with a catalyst such as palladium on carbon to afford II. As demonstrated in subsequent schemes, compounds of Formula II are key intermediates used in the synthesis of the purines, pyrimidines and their heterocyclic isosteres disclosed in this application.

According to one method (Scheme III), the compound of formula $I_A$ (or $I_B$ or II) is condensed with 2-amino-4,6-dichloropyrimidine in the presence of a tertiary amine base to afford the pyrimidine of formula 11. This compound is, in turn, converted to the pyrimidine of formula 13 by way of azo coupling with 4-chlorobenzenediazonium chloride and reduction with zinc in acetic acid. (Alternatively, the amino group can be introduced by reduction of the corresponding nitro-substituted pyrimidine). The purine of formula 14 is then prepared by treatment of the pyrimidine of formula 13 with triethyl orthoformate, or preferably, diethoxymethyl acetate, followed by ammonia in methanol and then a protic acid in methanol. Compounds of formula III are obtained by treatment of the compound of formula 14 with various nucleophiles. For instance, treatment of the compound of formula 14 with aqueous acid affords the compounds of formula III in which J=OH; alternately, treatment of the compound of formula 14 with ammonia in an alcoholic solvent affords the compounds of formula III in which $J=NH_2$; alternately, treatment of the compound of formula 14 with hydrogen in the presence of a noble metal catalyst affords the compounds of formula III in which J=H.

According to one method (Scheme IV), the compound of formula $I_A$ ($I_B$ or II) is condensed with 5-amino-4,6-dichloropyrimidine in the presence of a tertiary amine base to afford the pyrimidine of formula 15. The compound of formula 15 is treated with triethylorthoformate and acid, or preferably diethyloxymethyl acetate followed by ammonia in methanol followed by a protic acid in methanol to afford the pyrimidine of formula 16. This compound is, in turn, converted into purines of the formula IV by the methods outlined above in Scheme III for the conversion of purines of the formula 14 into purines of the formula III.

According to one method (Scheme V), the compound of formula $I_A$ (or $I_B$ or II) is sequentially treated with t-butyl dimethylsilyl chloride, trimethylsilyl isocyanate and silica gel to afford the compound of formula 20. This compound is in turn condensed with either (E)-3-ethoxyacryloyl chloride or (E)-3-methoxy-2-methylpropenoyl chloride to afford the compounds of formula 21. These compounds are treated with either aqueous acid or base to cause cyclization to compounds of the formula $V_{A-F}$. These compounds are in turn treated at elevated temperature with hexamethyldisilazane and formamide to afford the compounds of the formula $V_{G-L}$.

According to one method (Scheme VI), compounds of the formula 22, in which A is purin-9-yl, a heterocyclic isostere of a purin-9-yl group, a pyrimidin-1-yl group or a heterocyclic isostere of a pyrimidin-1-yl group as defined for Formula I, are protected at the 2'-hydroxymethyl group to afford compounds of the formula 23, in which TBS may represent any protecting group. In the preferred example, compounds of the formula 22 are treated with t-butyldimethylsilyl chloride (TBS-Cl) to afford compounds of the formula 23 in which TBS represents t-butyldimethylsilyl. Compounds of the formula 23 are then treated with methanesulfonyl chloride to afford compounds of the formula 24. These compounds are, in turn, treated with various nucleophiles and then deprotected. In the preferred example, in which TBS is t-butyldimethylsilyl, the protecting group is removed by trimethylsilyl chloride in methanol. When the nucleophile is azide, X in the compound of formula 25 is azido; when the nucleophile is a halide, X is halo; when the nucleophile is cyanide, X is cyano. Treatment of the compound of the formula VI when X is bromo with tri-n-butyl tin hydride affords the compound of the formula 25 in which X is H.

According to one method (Schemes VII, VIII and IX), compounds of the formulas 22, 25 and 26, in which A is as defined in Scheme VI, are treated with acylating agents such as an acid chloride or acid anhydride to afford compounds of the formulas VII, VIII and IX wherein $R_{50}$ is a straight or branched chain alkyl group (such as methyl or t-butyl), or a cycloalkyl group, or an aryl (such as phenyl, benzyl).

SCHEME I

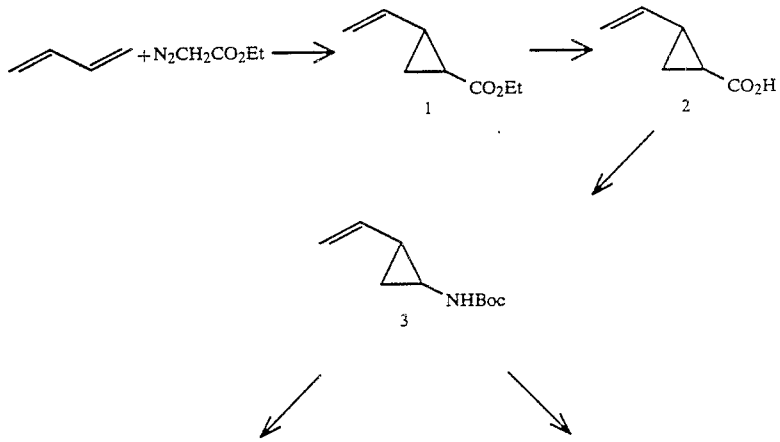

SCHEME I
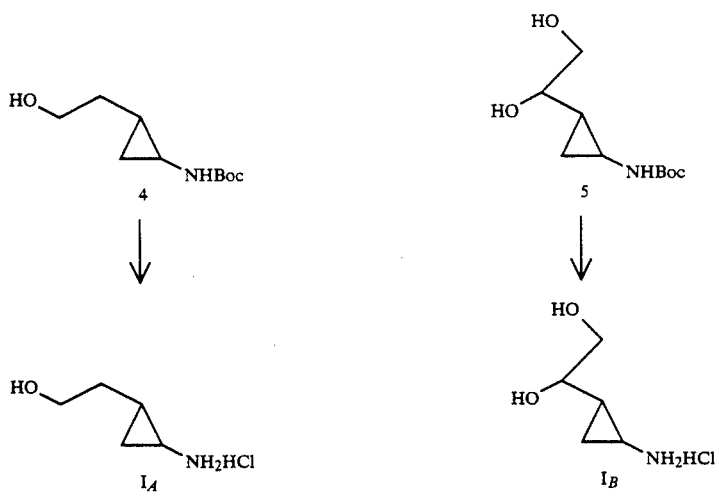
SCHEME II
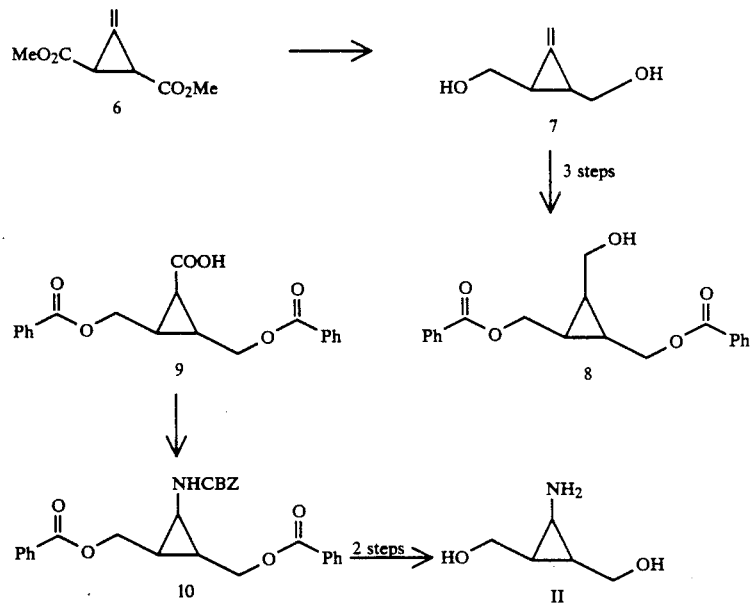
SCHEME III
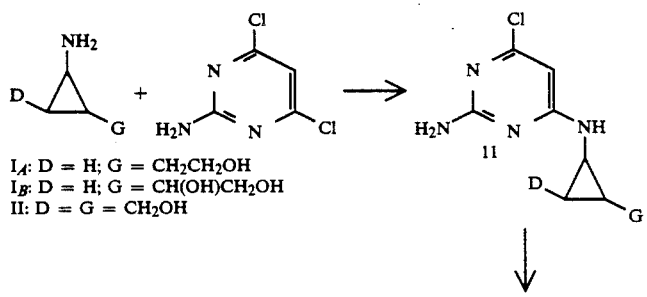
$I_A$: D = H; G = CH₂CH₂OH
$I_B$: D = H; G = CH(OH)CH₂OH
II: D = G = CH₂OH

SCHEME III

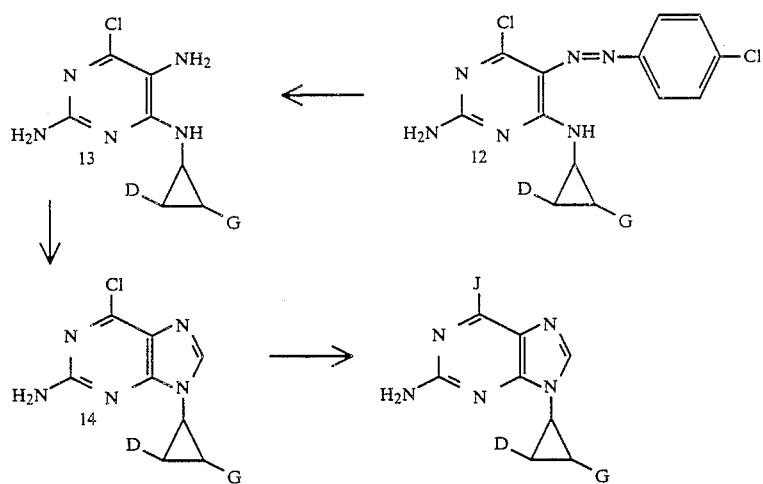

III<sub>A</sub>: D = H; G = CH₂CH₂OH
III<sub>B</sub>: D = H; G = CH(OH)CH₂OH
III<sub>C</sub>: D = G = CH₂OH

SCHEME IV

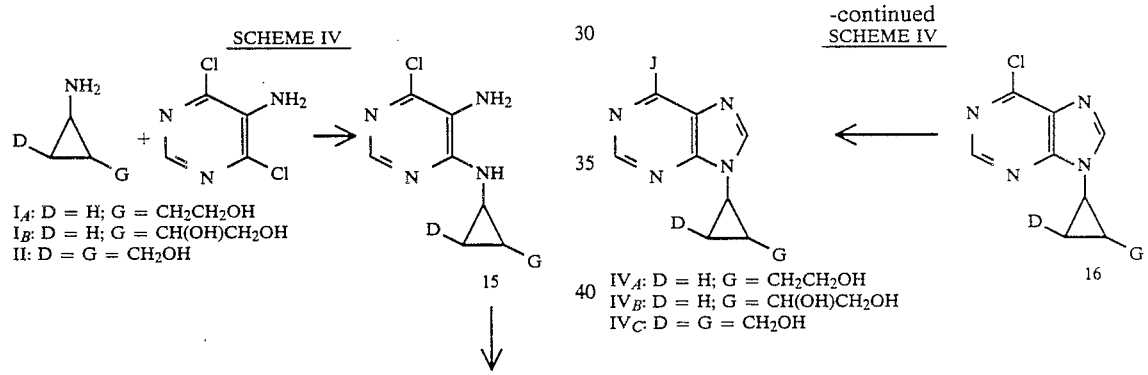

I<sub>A</sub>: D = H; G = CH₂CH₂OH
I<sub>B</sub>: D = H; G = CH(OH)CH₂OH
II: D = G = CH₂OH IV<sub>A</sub>: D = H; G = CH₂CH₂OH
IV<sub>B</sub>: D = H; G = CH(OH)CH₂OH
IV<sub>C</sub>: D = G = CH₂OH

SCHEME V

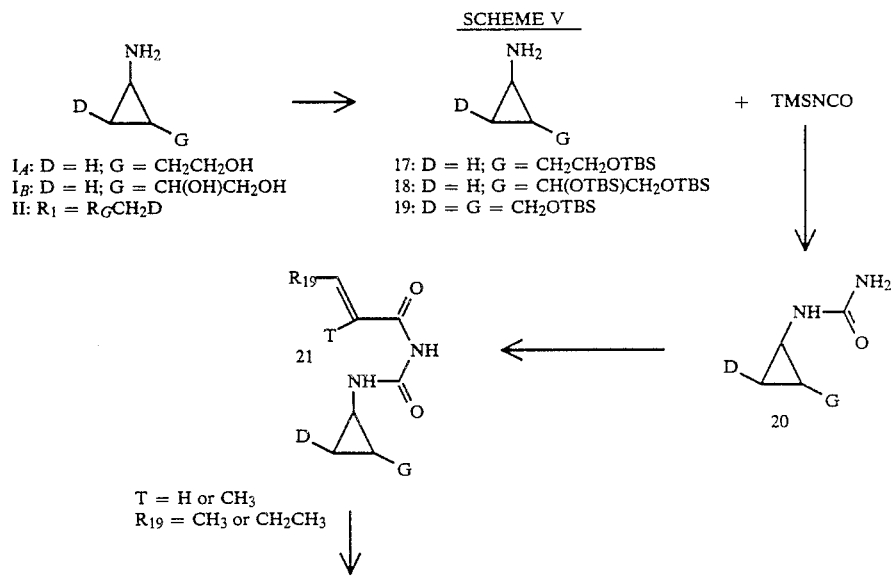

I<sub>A</sub>: D = H; G = CH₂CH₂OH
I<sub>B</sub>: D = H; G = CH(OH)CH₂OH
II: R₁ = R<sub>G</sub>CH₂D

17: D = H; G = CH₂CH₂OTBS
18: D = H; G = CH(OTBS)CH₂OTBS
19: D = G = CH₂OTBS

T = H or CH₃
R₁₉ = CH₃ or CH₂CH₃

SCHEME V
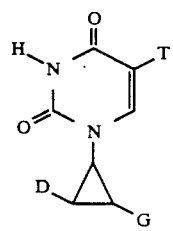  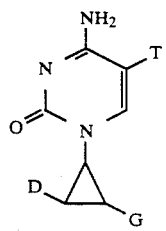
$V_A$: D = H; G = CH$_2$CH$_2$OH; T = H
$V_B$: D = H; G = CH$_2$CH$_2$OH; T = H
$V_C$: D = H; G = CH(OH)CH$_2$OH; T = H
$V_D$: D = H; G = CH(OH)CH$_2$OH; T = CH$_3$
$V_E$: D = G = CH$_2$OH; T = H
$V_F$: D = G = CH$_2$OH; T = CH$_3$
$V_G$: D = H; G = CH$_2$CH$_2$OH; T = H
$V_H$: D = H; G = CH$_2$CH$_2$OH; T = H
$V_I$: D = H; G = CH(OH)CH$_2$OH; T = H
$V_J$: D = H; G = CH(OH)CH$_2$OH; T = CH$_3$
$V_K$: D = G = CH$_2$OH; T = H
$V_L$: D = G = CH$_2$OH; T = CH$_3$
SCHEME VI
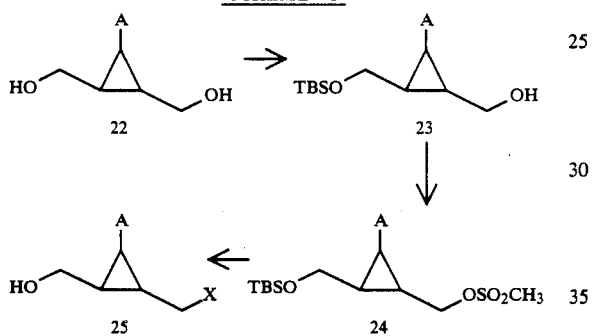
SCHEME VIII
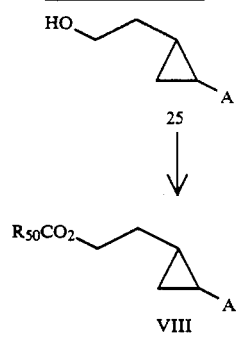
SCHEME IX
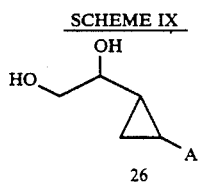
SCHEME VII
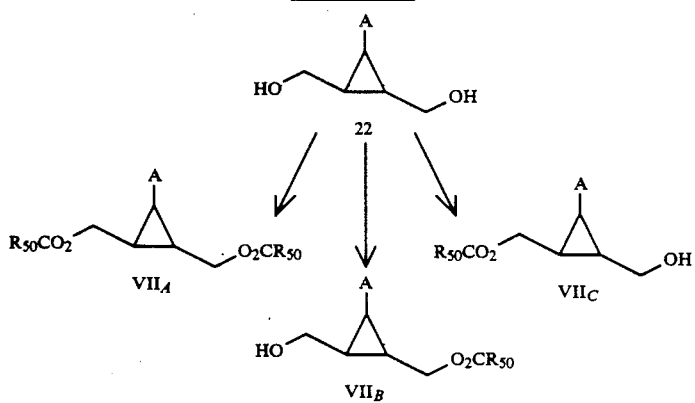

-continued
SCHEME IX

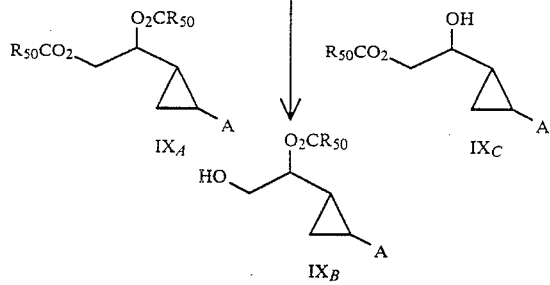

Useful intermediates for the preparation of compounds of the invention include compounds of the formula:

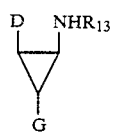

wherein G and D are independently selected from hydrogen, $C_1$ to $C_{10}$ alkyl and substituted derivatives thereof, —OH, —C(O)H, —$CO_2R_1$ wherein $R_1$ is hydrogen or $C_1$ to $C_{10}$ alkyl and —$OCH_2PO_3H_2$, with the proviso that one of D or G is other than hydrogen or $C_1$ to $C_{10}$ alkyl; and $R_{13}$ is hydrogen or an N-protecting group.

Other useful intermediates for the preparation of the compounds of the invention include compounds of the formula:

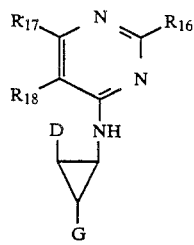

wherein G and D are independently selected from hydrogen, $C_1$ to $C_{10}$ alkyl and substituted derivatives thereof, —OH, —C(O)H, —$CO_2R_1$ wherein $R_1$ is hydrogen or $C_1$ to $C_{10}$ alkyl and —$OCH_2PO_3H_2$, with the proviso that one of D or G is other than hydrogen or $C_1$ to $C_{10}$ alkyl;

$R_{16}$ is hydrogen, —$NH_2$ or —OH;
$R_{17}$ is —OH or halogen; and
$R_{18}$ is —$NO_2$ or —$NH_2$.

Other useful intermediates for the preparation of compounds of the invention include compounds of the formula:

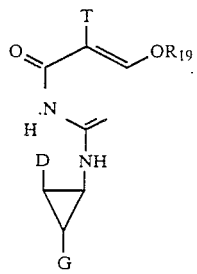

wherein G and D are independently selected from hydrogen, $C_1$ to $C_{10}$ alkyl and substituted derivatives thereof, —OH, —C(O)H, —$CO_2R_1$ wherein $R_1$ is hydrogen or $C_1$ to $C_{10}$ alkyl and —$OCH_2PO_3H_2$, with the proviso that one of D or G is other than hydrogen or $C_1$ to $C_{10}$ alkyl;

T is hydrogen, $C_1$ to $C_{10}$ alkyl, haloalkyl, hydroxyalkyl, azidoalkyl, halogen, cyano, nitro, alkenyl, haloalkenyl, cyanoalkenyl, alkoxycarbonylalkenyl, alkynyl, formyl, —$NR_1R_2$ wherein $R_1$ and $R_2$ are as defined above, —NHOH, —SH,

wherein m is 1 to 5, wherein m is 1 to 5, or —$CH_2NR_{12}R_2$ wherein $R_{12}$ and $R_2$ are as defined above; and $R_{19}$ is $C_1$ to $C_6$ alkyl.

Other useful intermediates for the preparation of the compounds of the invention include compounds of the formula:

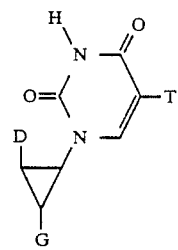

wherein G and D are independently selected from hydrogen, $C_1$ to $C_{10}$ alkyl and substituted derivatives thereof, —OH, —C(O)H, —$CO_2R_1$ wherein $R_1$ is hydrogen or $C_1$ to $C_{10}$ alkyl and —$OCH_2PO_3H_2$, with the proviso that one of D or G is other than hydrogen or $C_1$ to $C_{10}$ alkyl;
and and T is hydrogen, $C_1$ to $C_{10}$ alkyl, haloalkyl, hydroxyalkyl, azidoalkyl, halogen, cyano, nitro, alkenyl, haloalkenyl, cyanoalkenyl, alkoxycarbonylalkenyl, alkynyl, formyl, —$NR_1R_2$ wherein $R_1$ and $R_2$ are as defined above, —NHOH, —SH,

-continued
wherein m is 1 to 5, wherein m is 1 to 5, or —CH$_2$NR$_{12}$R$_2$ wherein R$_{12}$ and R$_2$ are as defined above.

The following examples will serve to further illustrate preparation of the novel compounds of the invention.

EXAMPLE 1

9-[2'-(2''-Hydroxyethyl)cyclopropyl]adenine

STEP A: Ethyl 2-ethenylcyclopropane carboxylate

Butadiene (200 mL) was liquified at −70° C. and added to ethyl diazoacetate (20 g, 175 mmol) in a pressure vessel. The catalyst, rhodium (II) acetate dimer (300 mg, 0.7 mmol), was added and the reaction vessel sealed. The reaction mixture was allowed to warm to ambient temperature and the reaction vessel was shaken for 24 h at ambient temperature. The reaction mixture and the ethanol rinse of the reaction vessel were combined and this blue solution was filtered through 50 g of silica gel. The silica gel was washed with 2% diethyl ether in pentane until the blue color was eluted. The blue solution was then concentrated in vacuo at 0° C. and filtered through CeliteR filter aid to remove any remaining catalyst. The filtrate was distilled under reduced pressure (approximately 15 mm) to yield 18.6 g (76% yield) of ethyl 2-ethenylcyclopropane carboxylate as a clear colorless liquid, b.p. 22°–26° C.

STEP B: 2-Ethenylcyclopropanecarboxylic acid

Ethyl 2-ethenylcyclopropyl carboxylate (12.1 g, 80.4 mmol) from Step A was dissolved in 15 mL of tetrahydrofuran (THF). An aqueous solution of 7.5 g of potassium hydroxide (dissolved in 70 mL of water) was added to the THF solution of the ethyl ester. The reaction mixture was heated to reflux (85° C.), under a nitrogen atmosphere, and refluxed for 5 h. TLC analysis (on silica gel plates eluted with 25% ethyl acetate in hexane) showed that all of the 2-ethenylcyclopropyl ester had been consumed in the reaction. The reaction mixture was then concentrated in vacuo to a white solid which was dissolved in water. The aqueous solution was extracted with diethyl ether to remove any residual ester starting material and then acidified with concentrated hydrochloric acid to free the acid from its potassium salt. The acidified solution was extracted with diethyl ether and the ether solution dried over anhydrous magnesium sulfate and filtered. The ether was removed by distillation and collected in a dry ice-acetone trap. Residual ether was removed by blowing nitrogen through the flask containing the product. 2-Ethenylcyclopropanecarboxylic acid was obtained in quantitative yield as a clear oil.

STEP C:
N-tert-Butoxycarbonyl-2-ethenylcyclopropylamine

2-Ethenylcyclopropanecarboxylic acid (14.42 g, 129 mmol) from Step B was dissolved in 100 mL of toluene at 0° C. Triethyl amine (19.79 mL) was added in one portion, followed by 30.5 mL of diphenylphosphonoazide (DPPA) added dropwise from an addition funnel. After the addition of DPPA was complete the reaction mixture was warmed to 70° C. and stirred at 70° C. for 45 minutes. tert-Butyl alcohol (50 mL) was added in one portion to the reaction mixture. The temperature of the reaction mixture was then raised to 100° C. and it was stirred overnight at this temperature. TLC analysis (on silica gel plates eluted with 25% ethyl acetate in hexane) showed no remaining starting material. The reaction mixture was diluted with 150 mL of methylene chloride, washed with 100 mL of 1M aqueous phosphoric acid solution, 100 mL of saturated sodium bicarbonate solution and 100 mL of saturated sodium chloride solution (brine), dried over anhydrous magnesium sulfate, filtered and concentrated in vacuo. The crude product was purified by column chromatography on silica gel eluted with 5% ethyl acetate in hexane. N-tert-Butoxycarbonyl-2-ethenylcyclopropylamine was obtained in 38% yield (8.97 g) as a clear colorless oil. $^1$H NMR (CDCl$_3$) 0.90 (m, 2H), 1.45 (s, 9H), 1.5 (m, 1H), 2.50 (m, 1H), 4.97 (dd, 1H), 5.07 (dd, 1H), 5.51 (m, 1H).

STEP D:
N-tert-Butoxycarbonyl-2-(2'-hydroxyethyl)cyclopropylamine

N-tert-Butoxycarbonyl-2-ethenylcyclopropylamine (3.96 g, 21.6 mmol) from Step C was dissolved in 21 mL of tetrahydrofuran (THF). A 1M solution of borane THF.complex in THF (43.27 mL, 2 equivalents) was added at 0° C. under a nitrogen atmosphere. After the reaction mixture was stirred at 0° C. for 2.5 h, TLC analysis (on silica gel plates eluted with 25% ethyl acetate in hexane) showed the presence of starting material. A second aliquot (2 mL) of the borane-THF solution was added. The reaction mixture was allowed to warm to ambient temperature and stirred at ambient temperature for 0.5 h then cooled to 0° C. again. A 6N aqueous solution of sodium hydroxide (25.1 mL, 3.5 equivalents) was added to the reaction mixture followed by 30% aqueous hydrogen peroxide solution (7.6 mL, 1.5 equivalents) and the resultant solution was stirred at 0° C. for 10 minutes. The reaction mixture was again allowed to warm to ambient temperature and stirred at ambient temperature for 1.5 h. Anhydrous potassium carbonate was added as a solid. The reaction mixture was then diluted with 100 mL of ethyl acetate, washed with 100 mL of 1N aqueous phosphoric acid solution, 100 mL of saturated sodium bicarbonate solution, dried over anhydrous magnesium sulfate and concentrated in vacuo. Flash chromatography on silica gel with solvent gradient elution of from 1% methanol in chloroform, initially, to a final concentration of 2% methanol in chloroform yielded 4.37 g (100% yield) of N-tert-butoxycarbonyl-2-(2'-hydroxyethyl)cyclopropylamine. CDI NH$_3$ MS, M/Z: 202 (M+H)$^+$.

STEP E: 2-(2'-Hydroxyethyl)cyclopropylamine hydrochloride

N-tert-Butoxycarbonyl-2-(2'-hydroxy)ethylcyclopropylamine (2.27 g, 11.3 mmol), from Step D, was dissolved in 40 mL of THF. To this solution at ambient temperature, was added 4 mL of 6N aqueous hydrochloric acid solution. After stirring the reaction mixture for 1 h at ambient temperature, TLC analysis (silica gel plates eluted with 2% methanol in chloroform) showed that all of the starting material had been consumed in the reaction. The amine salt product was taken on to Step F in solution without further purification.

STEP F:
1-((5'-Amino-6'-chloropyrimidin-4'-yl)amino)-2-(2''-hydroxyethyl)cyclopropane The solution of 2-(2'-hydroxy)ethylcyclopropylamine hydrochloride from Step E was concentrated in vacuo. Triethylamine (40 mL), butyl alcohol (100 mL) and 5-amino-4,6-dichloro- pyrimidine (3.70 g, 22.6 mmol) were added at ambient temperature and the reaction mixture was heated to 120° C. under a nitrogen atmosphere. The reaction mixture was stirred under nitrogen for approximately 30 h at 120° C. According to the TLC analysis (on silica gel plates eluted with 10% methanol in chloroform), the reaction was complete. The reaction mixture was concentrated in vacuo and purified by column chromatography on silica gel eluted with a gradient of from 2% to 5% methanol in chloroform. 1-(5'-amino-6'-chloropyrimidin-4'-yl)amino)-2-(2''-hydroxyethyl)cyclopropane was obtained in 42.6% yield (1.1 g), based on the hydrochloride salt, as a white solid, m.p. 153°–155° C. DCI NH$_3$ MS, M/Z: 229 (M+H)+

STEP G:
1-(6'-Chloro-9'H-purin-9'-yl)-2-(2''-hydroxyethyl)cyclopropane 1-((5'-Amino-6'-chloropyrimidin-4'-yl)amino)-2-(2''-hydroxyethyl)cyclopropane (1.1 g, 4.8 mmol) from Step F, triethyl orthoformate (11.39 g, 76.9 mmol) and 1.2 equivalents of concentrated hydrochloric acid solution (37.5%) were combined at ambient temperature under a nitrogen atmosphere. The reaction mixture was stirred at ambient temperature, under nitrogen, for 2 h. TLC analysis (on silica gel plates eluted with 10% methanol in chloroform) showed that the reaction had gone to completion with the formation of a single product. Solid anhydrous sodium bicarbonate was added to the reaction mixture along with 100 mL of water. The resultant aqueous solution was extracted with ethyl acetate and the organic layer was dried over anhydrous magnesium sulfate, filtered and concentrated in vacuo. TLC analysis (on silica gel plates eluted with 2% methanol in chloroform) showed the presence of three products. The three products were separated by column chromatography on a silica gel column eluted with a gradient of from 1% to 2% methanol in chloroform. The desired product, 1-(6'-Chloro-9'H-purin-9'-yl)-2-(2''-hydroxy)ethylcyclopropane was obtained in 54% yield (615.7 mg) and carried on to Step H.

STEP H: 9-[2'-(2''-Hydroxyethyl)cyclopropyl]adenine 1-(6'-Chloro-9'H-purin-9'-yl)-2-(2''-hydroxy)ethylcyclopropane (615.7 mg, 2.59 mmol) from Step G was dissolved in liquid ammonia in a pressure vessel. The vessel was heated to 78° C. and shaken for 18 h. The reaction mixture was then concentrated and purified by column chromatography on a silica gel column eluted with 10% methanol in chloroform. The desired product, 9-[2'-(2''-Hydroxy)ethylcyclopropyl]adenine, was obtained in 18.8% yield (107 mg) as a white solid, m.p. 179°–181.5° C.DCI NH$_3$ MS, M/Z: 220 (M+H)+.$^1$H NMR (CD$_3$OD) 1.06 (m, 1H), 1.39 (m,3H), 2.00 (m, 1H), 3.37 (m,1H), 3.88 (m, 2H), 8.10 (s, 1H), 8.22 (s, 1H).

EXAMPLE 2

9-[2-(2'-Hydroxy)ethylcyclopropyl]guanine

STEP A:
1-((2'-amino-6'-chloropyrimidin-4'-yl)amino)-2-(2''-hydroxyethyl)cyclopropane The product of Example 1, Step D, N-tertbutoxycarbonyl-2-(2'-hydroxyethyl)cyclopropylamine (1.45 g, 7.2 mmol) was dissolved in 45 mL of THF. Aqueous 6N hydrochloric acid solution was added and the reaction mixture was stirred at ambient temperature for one hour then concentrated under reduced pressure. At this time, 40 mL of triethyl amine, 40 mL of butyl alcohol and 2.36 g (2 equivalents) of 2-amino-4,6-dichloropyrimidine were added to the reaction mixture and it was heated to 120° C., under a nitrogen atmosphere. The reaction mixture was stirred overnight at 120° C., under nitrogen. TLC analysis (on silica gel plates eluted with 10% methanol in chloroform) showed that the reaction had gone to completion. The reaction mixture was diluted with 100 mL of water and extracted with ethyl acetate. The organic layer was dried over anhydrous magnesium sulfate, filtered and concentrated in vacuo. The crude product was purified by column chromatography on a silica gel column eluted with a solvent gradient from 1% to 2% methanol in chloroform. The desired product, 1-(2'-amino-6'-chloropyrimidin-4'-yl)amino)-2-(2''-hydroxyethyl)-cyclopropane, was obtained in 94% yield (1.54 g) as a white solid, m.p. 136°–139° C.

STEP B:
1-[[2'-Amino-5'-((4''-chlorophenyl)diazo)-6'-chloropyrimidin-4'-yl]amino]-2-(2'''-hydroxyethyl)cyclopropane A solution of 4-chlorobenzenediazonium chloride was prepared by combining 0.9 g (7.15 mmol) of p-chloroaniline, an aqueous solution of 0.4 g of sodium nitrite in 4.5 mL of water and 5.8 mL of 12N hydrochloric acid solution at 0° C. and stirring for 20 minutes at 0° C. The solution of 4-chlorobenzenediazonium chloride was added dropwise to an aqueous solution of 1-((2'-amino-6'-chloro-4'-pyrimidinyl)amino)-2-(2'-hydroxyethyl)cyclopropane, from Step A, containing 8.43 g (61.96 mmol) of sodium acetate and 24 mL of acetic acid in 24 mL of water. The reaction mixture was stirred overnight at ambient temperature. A yellow-orange colored precipitate formed after 1 h. After approximately 18 h, the reaction mixture was cooled and filtered. The desired product, 1-[[2'-Amino-4'-((4''-chlorophenyl)diazo)-6'-chloropyrimidin-4'-yl]amino]-2-(2'''-hydroxyethyl)cyclopropane, was collected as a yellow-orange colored solid (820 mg) in 47% yield. DCI NH$_3$ MS, M/Z: 367 (M+H)+.

STEP C:
1-(2',5'-Diamino-6'-chloropyrimidin-4'-yl)amino-2-(2''-hydroxyethyl)cyclopropane 1-[[2'-Amino-4'-((4''-chlorophenyl)diazo)-6'-chloropyrimidin-4'-yl]amino]-2-(2'''-hydroxyethyl)cyclopropane (0.63 g, 1.72 mmol) from Step B, glacial acetic acid (1 mL), ethanol (25 mL), water (25 mL) and zinc (1.4 g, 21.5 mmol) were combined at ambient temperature. The suspension was brought to reflux temperature and after refluxing for 1 h, TLC analysis (on silica gel plates eluted with 10% methanol in chloroform) showed that only 10% of the starting material had been converted to product. More zinc and acetic acid were added and the reaction mixture immediately became clear and dark brown in color. After stirring for 5 minutes the reaction mixture was again sampled for TLC analysis. This time the reaction was complete. The reaction mixture was cooled and extracted with diethyl ether to remove para-chloroaniline. The aqueous layer was concentrated and the residue was purified by column chromatography on silica gel eluted with a gradient of methanol in chloroform, from 1% to 5% methanol. 1-[(2',4',5'-Diamino-6'-chloropyrimidin-4'- yl)amino]-2-(2''-hydroxyethyl)cyclopropane was obtained as a white solid, m.p. 186°–191° C. DCI NH$_3$ MS, M/Z: 244 (M+H)+.

STEP D:
1-(2'-Amino-6'-chloro-9'H-purin-9'-yl)-2-(2''-hydroxyethyl)cyclopropane The product of Step C (176.9 mg, 0.73 mmol) was dissolved in 16 equivalents (1.72 g, 11.62 mmol) of triethylorthoformate. Concentrated (37%) aqueous hydrochloric acid (0.07 mL, 1.2 equivalents) was added in one portion at ambient temperature. The reaction mixture was stirred at ambient temperature for 1 h. During this time the solution became cloudy. The reaction mixture was concentrated in vacuo and purified by column chromatography on silica gel eluted with 5% methanol in chloroform. The desired product, 1-(2'-amino-6'-chloro-9'H-purin-9'-yl)amino-2-(2''-hydroxyethyl)cyclopropane, was obtained from fractions 39-42 as a white solid (0.165 g, 90% yield), m.p. 190°–192° C. DCI NH$_3$ MS, M/Z: 254 (M+H)+.

STEP E: 9-2'-(2''-Hydroxyethyl)cyclopropyl guanine

The product of Step D (103 mg, 0.4 mmol) was dissolved in 25 mL of 0.5N aqueous sodium hydroxide solution. The reaction mixture was heated to 120° C. and stirred at 120° C. for 2h. TLC analysis showed that the starting material had been consumed in the reaction. The aqueous reaction mixture was extracted with methylene chloride to remove any residual starting material not detected by TLC analysis and adjusted to pH 8.5. A copious precipitate was formed. The reaction mixture was cooled and the precipitate collected by filtration and washed with cold water. The yellow solid was purified by column chromatography on silica gel eluted with a gradient of 10% methanol in chloroform to 20% methanol in chloroform. The desired product, 9-[2-(2'-hydroxyethyl)cyclopropyl]guanine, was obtained from fractions numbered 8–13, m.p. >250° C. DCI NH$_3$ MS, M/Z: 236 (M+H)+. The 300 MHz $^1$H NMR (D$_6$-DMSO) 0.81 (m, 1H), 1.15 (m, 1H), 1.31 (m,1H), 1.43 (m,1H), 1.55 (m,1H), 3.04 (m, 1H), 4.79 (m,1H), 6.41 (m, 2H), 7.59 (s, 1H).

EXAMPLE 3

9-2-(1',2'-Dihydroxyethyl)cyclopropyl guanine

STEP A:
N-tert-Butoxycarbonyl-2-(1',2'-dihydroxy)ethylcyclopropyl amine

Sodium hydroxide solution (114 mg in 10 mL of water) was added to N-tert-butoxycarbonyl-2-ethenylcyclopropylamine (59 mg, 0.3 mmol), from Step C of Example 1, until the N-tert-butoxycarbonyl-2-ethenylcyclopropylamine oiled out to form a separate organic layer. THF (10 mL) was added until a cloudy solution was formed. An additional 2.5 mL of water was added and the solution became clear. The clear colorless solution was cooled to 0° C. in an ice-water bath. A solution of potassium permanganate (80 mg, 0.5 mmol) in 10 mL of water was added and the cold reaction mixture was stirred vigorously for 5 minutes at 5° C. TLC analysis (on silica gel plates eluted with 25% ethyl acetate in hexane) showed that all of the starting material had been consumed in the reaction. The reaction mixture was concentrated in vacuo and the residue dissolved in water. The resultant aqueous solution was extracted 3 times with ethyl acetate. The combined ethyl acetate layers were dried over anhydrous sodium sulfate and concentrated in vacuo. N-tert-Butoxycarbonyl-2-(1',2'-dihydroxyethyl)cyclopropyl amine was obtained in 86% crude yield (56 mg) as a clear colorless oil. The crude product was carried on to Step B without further purification. DCI NH$_3$ MS, M/Z: 218 (M+H)+, 235 (M+NH$_4$)+.

STEP B: 2-(1',2'-Dihydroxyethyl)cyclopropylamine

N-tert-Butoxycarbonyl-2-(1',2'dihydroxyethyl)cyclopropylamine (0.49 g, 2.2 mmol) from Step A was dissolved in 1.7 mL (23 mmol) of trifluoroacetic acid (TFA) in a 250 mL round bottom flask. TLC analysis of the resultant yellow solution (on silica gel plates eluted with ethyl acetate) showed that the starting material had been consumed in the reaction. The solution was concentrated in vacuo and the residue dissolved in 20 mL of methanol. Rexyn 201$^R$ hydroxide resin was added to the methanol solution with stirring at ambient temperature until the solution was basic to pH paper. The resin was filtered and the filtrate was concentrated in vacuo. 2-(1',2'-dihydroxyethyl)cyclopropylamine was obtained in quantitative yield as a yellow oil and used in Step C without further purification. DCI NH$_3$ MS, M/Z: 118 (M+H)+, 135 (m+NH$_4$)+.

STEP C:
1-((2'-Amino-6'-chloropyrimidin-4'-yl)amino)-2-(1',2'-dihydroxyethyl)cyclopropane 2-(1',2'-Dihydroxyethyl)cyclopropylamine from Step B was dissolved in 30 mL of n-butyl alcohol. Triethylamine (3.5 mL, 25 mmol) was added, followed by 1.1 g (6.6 mmol) of 2-amino-4,6-dichloropyrimidine. The reaction mixture was heated to reflux temperature (130° C.), with stirring, under a nitrogen atmosphere and was refluxed for approximately 48 h. TLC analysis on silica gel plates eluted with 50% methanol in chloroform showed total disappearance of the amine starting material and TLC analysis on silica gel plates eluted with 10% methanol in chloroform showed the formation of the product. The reaction mixture was concentrated in vacuo and the residue was taken up in a biphasic mixture of water and chloroform. The layers were separated and the aqueous layer was washed with chloroform. The combined chloroform layers were washed twice with water and discarded. The aqueous layers were combined, mixed with a small amount of acetonitrile (to act as an antifoaming agent) and concentrated in vacuo. The dark red solid residue was dissolved in 50 mL of methanol and Rexyn 201$^R$ hydroxide resin was added with stirring at ambient temperature, under a nitrogen atmosphere, until the solution tested alkaline on pH paper. The resin was filtered and the filtrate concentrated in vacuo to a dark red oil. The crude product was purified by crystallization from 10% methanol in chloroform solution. In the first precipitate, 302 mg of 1-((2'-amino-6'-chloropyrimidin-4'-yl)amino)-2-(1',2'-dihydroxyethyl)cyclopropane was obtained as a beige colored solid, m.p. 124°–130° C. A second crop obtained from the mother liquor yielded an additional 58 mg of the desired product as a beige colored solid. The mother liquor was concentrated in vacuo and chromatographed on 35 g of silica gel eluted with a gradient of 5% methanol in chloroform to 25% methanol in chloroform. The methanol concentrated was increased in steps from 5% to 7% to 10% to 15% to 25%. This procedure yielded an additional 325 mg of the desired product as a pale yellow solid. The total yield of 1-((2'- amino-6'-chloropyrimidin-4'-yl)amino)-2-(1',2'-dihydroxyethyl)cyclopropane was 685 mg (47%). DCI NH$_3$ MS, M/Z: 245 (M+H)+.

STEP D:
1-[[2'-Amino-5'-((4''-chlorophenyl)diazo)-6'-chloropyrimidin-4'-yl]amino]-2-(1''',2''''dihydroxy)ethylcyclopropane A suspension of 4-chloroaniline (0.36 g, 2.8 mmol) in 3 mL of water (in a 100 mL round bottom flask) was cooled to 0° C. in a ice-salt water bath. Concentrated (37%) hydrochloric acid (0.8 mL, 9.3 mmol) and aqueous sodium nitrite (210 mg in 3 mL of water) were added to the cooled suspension. The reaction mixture was stirred at 0° C. until it became a clear colorless solution of p-chlorobenzenediazonium chloride. 1-[(2'-Amino-6'-chloropyrimidin-4'-yl)amino]-2-(1',2'-dihydroxyethyl)cyclopropane (617 mg, 2.5 mmol) from Step C was dissolved in an aqueous buffered solution containing 12.5 mL of water, 12.5 mL of glacial acetic acid and 5 g of sodium acetate. This solution was added dropwise, through an addition funnel, into the flask containing the p-chlorobenzenediazonium chloride solution, at 0° C., over a 0.5 h period. The reaction mixture was allowed to warm to ambient temperature and was stirred at ambient temperature for approximately 18 h. The reaction mixture was filtered and the filter cake was washed with water then dried in vacuo at 45° C. for 45 minutes. 1-[2'-Amino-4'-(4''-chlorophenyl)-diazo-6'-chloropyrimidin-4'-yl]amino-2-(1''',2'''-dihydroxy)ethylcyclopropane was obtained (280 mg, 29% yield) as a yellow-orange colored solid, m.p. 220°–223° C. Additional product was obtained, for a total yield of 628 mg (65%), by adding additional (cold) p-chlorobenzenediazonium chloride solution to the filtrate and stirring the resultant solution at ambient temperature, filtering and washing the precipitate with water. DCI NH$_3$ MS, M/Z: 383 (M+H)+. The 300 MHz $^1$H NMR spectrum is consistent with the assigned structure.

STEP E:
1-(2',5'-Diamino-6'-chloropyrimidin-4'-yl)amino]-2-(1'',2''-dihydroxyethyl)cyclopropane 1-[[2'-Amino-5'-((4''-chlorophenyl)diazo)-6'-chloropyrimidin-4'-yl]amino]-2-(1''',2'''-dihydroxyethyl)cyclopropane (611 mg, 1.6 mmol) from Step D, 15 mL of ethanol, 15 mL of water and 1.5 mL of glacial acetic acid were combined to form a yellow suspension. The suspension was heated to 70° C. under a nitrogen atmosphere and three 383 mg portions of zinc dust were added with vigorous stirring at 5 minute intervals. The reaction mixture, a red solution, was stirred at 70° C. for 1 h under nitrogen. The golden-brown solution was cooled to ambient temperature in an ice water bath and filtered through Celite ® filter aid. The filter cake was washed with ethanol and the filtrate was concentrated in vacuo. The product and zinc acetate biproduct were co-precipitated from the filter cake in ethanol as a beige solid. This solid was combined with the concentrated filtrate and purified by column chromatography on 20 g of silica gel eluted with a step-gradient of methanol in chloroform. The percent methanol was varied from 2% to 4% to 6% to 8% to 10% to 15% to 20% to 30% to 40% and finally to 50% methanol in chloroform. The title compound was obtained in 75% yield (313 mg) as a red solid. This red solid was recrystallized from ethanol to yield 67 mg (16% yield) of pure 1-([2',5'-diamino-6'-chloropyrimidin-4'-yl)amino]-2-(1'',2''-dihydroxyethyl)cyclopropane as a light pink solid, m.p. 208–215 (with decomposition). DCI NH$_3$ MS, M/Z: 260 (M+H)+. The 300 MHz $^1$H NMR is consistent with the assigned structure.

STEP F:
1-(2'-Amino-6'-chloro-9'H-purin-9'-yl)-2-(1'',2''-dihydroxyethyl)cyclopropane 1-[(2',5'-Diamino-6'-chloropyrimidin-4'-yl)amino]-2-(1'',2''-dihydroxyethyl)cyclopropane (0.29 g, 1.1 mmol) from Setp E was dissolved in dimethyl formamide (DMF) under a nitrogen atmosphere. Triethylorthoformate (2.2 mL, 13.2 mmol) was added, followed by 0.1 mL of concentrated (37%) aqueous hydrochloric acid. The reaction mixture was stirred at ambient temperature, under nitrogen, for approximately 72 h, then concentrated in vacuo. The water was removed as an azeotrope of toluene and methanol to yield a red solid. TLC analysis (silica gel plates eluted with 10% methanol in chloroform) of the residue showed that the starting marterial had been consumed in the reaction. The red solid was dissolved in 50% aqueous acetic acid and the solution stirred at ambient temperature for 2.5 h then concentrated in vacuo. Ammonia was added to the residue as 50 mL of a 10% (vol/vol) solution of ammonia in methanol. The resultant solution was stirred at ambient temperature for 1.5 h then concentrated in vacuo to yield a mixture of a red syrup and a red solid. This crude mixture was taken on to Step G without further purification.

STEP G: 9-[2-(1',2'-dihydroxyethyl)cyclopropyl guanine 1-(2'-Amino-6'-chloro-9'H-purin-9'-yl)-2-(1'',2''-dihydroxyethyl)cyclopropane from Step F was dissolved in 20 mL of 2N hydrochloric acid. The reaction mixture was heated to reflux temperature (110° C.) with stirring, under a nitrogen atmosphere and refluxed for 5 h. TLC analysis (on silica gel plates eluted with 10% methanol in chloroform) showed that all of the starting material had been consumed in the reaction. The reaction mixture was concentrated under reduced pressure (using a water aspirator) to a dark red syrup. Residual water was removed as an azeotrope with ethanol. The solid residue was dissolved in 10 mL of water and the aqueous solution was filtered to remove insoluble impurities. The filtrate was then concentrated in vacuo to a solid residue which was redissolved in approximately 4 mL of water. The dark red solution was filtered through a glass wool plug and adjusted to approximately pH 7 with 5N sodium hydroxide. The solution was refrigerated for 1 h, during which time a brown precipitate formed. The precipitate was filtered and washed sequentially with water, ethanol and diethyl ether. TLC analyses of the filtrate and the precipitate (on silica gel plates eluted with 25% methanol in chloroform) indicated that the the desired product was present in the filtrate, not in the precipitate. The filtrate was concentrated in vauco and the residue redissolved in water. The aqueous solution was filtered through a glass wool plug to yield golden yellow colored filtrate which was concentrated in vacuo to a yellow colored solid. The solid was dissolved in approximately 3 mL of water and 10–15 mL of ethanol was added to this solution, followed by diethyl ether until the solution became cloudy. The solution was placed in the freezer to induce crystallization. Approximately 57 mg of yellow colored solid was collected by filtration. Additional solid was recovered from the mother liquor by concentrating it, adding ethanol and cooling. The combined precipitates were recrystallized twice from methanol in chloroform and once from methanol in diethyl ether to yield 66 mg of the title compound as a yellow colored solid, m.p. >250° C. DCI NH$_3$ MS, M/Z: 252 (M+H)$^+$.

EXAMPLE 4

9-[2-(1',2'-Dihydroxyethyl)cyclopropyl]adenine

STEP A:

1-[(5'-Amino-6'-chloropyrimidin-4'-yl)amino]-2-(1'',2''-dihydroxy)ethylcyclopropane 2-(1',2'-Dihydroxy)ethylcyclopropylamine (0.27 g, 2.3 mmol), from Step B of Example 3, 12 mL of n-butyl alcohol and 1.3 mL (4 equivalents) of triethylamine were combined in a 100 mL round bottom flask at ambient temperature. 5-Amino-4,6-dichloropyrimidine (0.75 g, 4.6 mmol) was added in one portion. The cloudy solution was heated to reflux temperature (130° C.) under a nitrogen atmosphere and refluxed for approximately 20 h. TLC analysis on silica gel plates eluted with 50% methanol in chloroform showed that the amine starting material had been consumed. TLC analysis on silica gel plates eluted with 15% methanol in chloroform indicated that the desired product had been formed. The reaction mixture was allowed to cool to ambient temperature and concentrated in vacuo. The dark red solid residue was dissolved in chloroform and the chloroform solution was washed three times with water. The combined aqueous washes were extracted once with chloroform. Rexyn 201 ® hydroxide resin was added to the combined aqueous extracts and this suspension was stirred at ambient temperature for 0.5 h. The resin was filtered and the filtrate concentrated in vacuo. The residue was purified by column chromatography on 8 g of silica gel eluted with a step gradient of methanol in chloroform. The percentage methanol in the solvent was varied from 5% to 10% to 15% to 20%. The fractions containing the desired product were combined and concentrated in vacuo to yield 0.39 g (69% yield) of 1-[(5'-amino-6'-chloropyrimidin-4-'yl)amino]-2-(1'',2''-dihydroxyethyl)cyclopropane as a foamy yellow syrup. which was taken on to Step B without further purification. DCI NH$_3$ MS, M/Z: 245 (M+H)$^+$. 1H NMR (CDCl3) 0.90 (m, 1H), 1.00 (m, 1H), 2.73 (m, 1H), 3.01 (m, 1H), 3.30 (t, 2H), 3.70 (m, 1H), 7.80 (d, 1H).

STEP B:

1-(6'-Chloropurin-9'-yl)-2-(1'',2''-dihydroxyethyl)cyclopropane

1-[(5'-Amino-6'-chloropyrimidin-4'-yl)amino]-2-(1'',2''-dihydroxyethyl)cyclopropane (95 mg, 0.39 mmol) from Step A was dissolved in 2 mL of dimethyl formamide (DMF) in a 100 mL round bottom flask. Triethylorthoformate (0.70 g, 4.7 mmol) was added to the solution, followed by 0.025 mL of concentrated (37%) aqueous hydrochloric acid. The reaction mixture was stirred at ambient temperature under a nitrogen atmosphere for 2 h. TLC analysis (on silica gel plates eluted with 10% methanol in chloroform) showed that starting material had been consumed in the reaction. The solvents were evaporated in vacuo and the water removed as an azeotrope with ethanol. The solid residue was dissolved in 10% (vol/vol) ammonia in methanol. The resultant solution was stirred at ambient temperature for approximately 16 h under a nitrogen atmosphere then concentrated in vacuo. The residue was purified by column chromatography on 10 g of silica gel eluted with a step gradient of methanol in chloroform. The percent of methanol in the solvent was increased from 5% to 10% to 15%. The fractions containing the desired product were combined and concentrated to yield 69 mg (70% yield) of 1-(6-chloropurin-9'-yl)-2-(1'',2''-dihydroxyethyl)cyclopropane as an off-white solid, m.p. 233°-235° C.

STEP C:

9-[2-(1',2'-Dihydroxyethyl)cyloopropyl]adenine 1-(6'-Chloropurin-9'-yl)-2-(1'',2''-dihydroxy)ethylcyclopropane (0.32 g, 1.2 mmol) from Step B was dissolved in 10 mL of ethanol in a pressure tube. Liquid ammonia (20 mL) was added to this solution and the tube was sealed. The tube containing the reaction mixture was shaken at 60° C. for approximately 60 h. The top of the tube was broken while the tube was in a dry ice-acetone bath and the tube was allowed to warm to room temperature in order to evaporate the ammonia from the reaction mixture. The ethanol was removed in vacuo and the residue redissolved in ethanol. The ethanol solution was filtered through a glass wool plug to remove insoluble impurities. The filtrate was concentrated in vacuo. The product was precipitated from ethanol/diethyl ether. The precipitate was recrystallized from methanol to give 9-[2-(1',2'-Dihydroxyethyl)cyclopropyl]adenine in 9% yield (25 mg) as a white crystals, m.p. 198°-203° C. Additional amounts of the title compound were obtained by chromatographic purification of the concentrated mother liquors. DCI NH$_3$ MS, M/Z: 236 (M+H)$^+$. $^1$H NMR (d$_6$-DMSO) 1.14 (m, 1H), 1.24 (m, 1H), 1.60 (m, 1H), 3.37 (m, 2H), 3.54 (m, 2H), 4.75 (d, 1H), 5.25 (t, 1H), 7.26 (bs, 2H), 8.08 (s, 1H), 8.13 (s, 1H).

EXAMPLE 5

9-[2-(1',2'-Diacetoxy)ethylcyclopropyl)guanine

To a stirred solution of 196 mg (0.78 mmol) of the product of Step G of Example 3 in 10 mL of acetonitrile is added 0.287 mL (2.06 mmol) of TEA, 7 mg (0.0585 mmol) of DMAP and 0.177 mL (1.87 mmol) of acetic anhydride. After 3 h at ambient temperature, the clear solution is treated with 1 mL of methanol, concentrated under reduced pressure, redissolved in 2mL of methanol and added to 50 mL of water. The precipitate is removed by filtration, washed with water and dried under vacuum at 60° C. to afford the title compound.

EXAMPLE 6

9-[(1'β,2'α,3'β)-Bis(hydroxymethyl)-cyclopropyl)]adenine

STEP A: Dimethyl (1α,2β)-3-methylen-1,2-cyclopropane dicarboxylate

3-Methylene-1,2-cyclopropanecarboxylic acid (commercially available from Aldrich Chemical Co.) (12 g 84.5 mmol), 1 mL of concentrated sulfuric acid and 200 mL of methanol were combined at ambient temperature and stirred together at ambient temperature for approximately 18 h. Solid sodium bicarbonate was added to the reaction mixture. The reaction mixture was then concentrated in vacuo and the residue dissolved in ethyl acetate. The ethyl acetate solution was washed with water and then sodium bicarbonate solution, dried over anhydrous magnesium sulfate and then concentrated in vacuo. The residue was purified by column chromatography on a 5×27 cm silica gel column eluted with 10% ethyl acetate in hexane. Dimethyl 3-methylene-1,2-cyclopropane dicarboxylate (13.1 g, 91.3% yield) was obtained from fractions numbered 6–8 as a clear, colorless, oily liquid.

STEP B:
(1α,2β)-3-Methylene-1,2-bis(hydroxymethyl)-cyclopropane

Dimethyl 3-methylene-1,2-cyclopropane dicarboxylate (12.9 g, 75.9 mmol) from Step A was dissolved in 50 mL of dry toluene. In a separate 1 L flask 253 mL (380 mmol) of 1.5M diisobutylaluminum hydridride (DIBAH) in toluene was cooled to −78° C. in a dry ice-acetone bath. The solution of dimethyl 3-methylene-1,2-cyclopropane dicarboxylate was added dropwise to the DIBAH solution, with stirring, over a 3 h period. The reaction mixture was stirred at −78° C. for 3 h and the reaction was quenched with 27.3 mL of methanol added dropwise to the reaction mixture at −78° C. The reaction mixture was stirred for approximately 10 min then 45.5 mL of water was added. The reaction mixture was allowed to slowly warm to ambient temperature, filtered and the precipitate washed with ethyl acetate. The washed precipitate was slurried with methanol and filtered until no organic product was detected in the filtrate. The combined organic filtrates were concentrated in vacuo and purified by column chromatography on a 3×57 cm silica gel column eluted with 5% methanol in chloroform followed by 10% methanol in chloroform. Fractions 43–87 were combined and concentrated under reduced pressure to yield 3-methylene-1,2-bis(hydroxymethyl)cyclopropane (5.15 g, 59.5% yield) as a clear colorless liquid.

STEP C:
(1α,2β)-3-Methylene-1,2-bis(benzoyloxymethyl)-cyclopropane

3-Methylene-1,2-bis(hydroxymethyl)cyclopropane (4.5 g, 39.5 mmol) was dissolved in 100 mL of methylene chloride. Pyridine (6.85 g, 86.8 mmol) was added to the solution followed by 11.1 g (78.9 mmol) of benzoyl chloride. The reaction mixture was stirred at ambient temperature for approximately 18 h. TLC analysis (silica gel plates eluted with 10% ethyl acetate in hexane) indicated that all of the alcohol starting material had been consumed in the reaction. The reaction mixture was diluted with water and methylene chloride. The two phases were separated and the organic layer was washed sequentially with 1N hydrochloric acid solution and dilute aqueous sodium bicarbonate solution, dried over anhydrous magnesium sulfate, filtered and concentrated in vacuo. The residue was purified by column chromatography on a 3×30 cm silica gel column eluted with 10% ethyl acetate in hexane. The fractions containing the desired product were combined and concentrated in vacuo to give 11.76 g (92% yield) of 3-Methylene-1,2-bis(benzoyloxymethyl)cyclopropane. DCI $NH_3$ MS, M/Z: 323 (M+H)+, 340 (M+$NH_4$)+. $^1$H NMR ($CDCl_3$) 2.03 (m, 2H), 5.62 (s, 2H), 7.30 (d, 4H), 7.53 (m, 2H), 8.0 (m, 4H) ppm.

STEP D:
(1α,2β,3α)-3-Hydroxymethyl-1,2-bis(benzoyl)oxymethyl)cyclopropane

A solution of 8.36 g (26 mmol) of 3-Methylene-1,2-bis(benzoyloxymethyl)cyclopropane (from Step C) in tetrahydrofuran (THF) was cooled in an ice-water bath. To this solution was added 26 mL (26 mmol) of a 1 M THF solution of borane-THF complex, and the resultant solution was stirred at 5° C. for 2 h. 3N Sodium hydroxide solution (8.67 mL, 26 mmol) was then added slowly to the reaction mixture at 5° C., followed by 7.8 mL (78 mmol) of 30% aqueous hydrogen peroxide solution. The reaction mixture was stirred for 20 min at 5° C., allowed to warm to ambient temperature and stirred for 30 min at ambient temperature. The reaction mixture was diluted with ethyl acetate, washed 3 times with brine (until the pH of the aqueous layer was approximately 7) and concentrated in vacuo. The residue was purified by column chromatography on a 3×65 cm silica gel column eluted with 2% methanol in chloroform. Fractions numbered 35–47 were combined and concentrated in vacuo to give 4.1 g (46% yield) of 3-Hydroxymethyl-1,2-bis((benzoyl)oxymethyl)cyclopropane. DCI $NH_3$ MS, M/Z: 341 (M+H)+, 358 (M+$NH_4$)+.

STEP E:
(1α,2β,3α-2,3-Bis(benzoyloxymethyl)-cyclopropylcarboxylic acid

3-Hydroxymethyl-1,2-bis((benzoyloxymethyl)-cyclopropane (3.55 g, 10.4 mmol) from Step D, was dissolved in a mixture of 20 mL of carbon tetrachloride, 20 mL of acetonitrile and 30 mL of water. Sodium periodate (6.67 g, 31.2 mmol) was added, followed by 50 mg (0.24 mmol) hydrated ruthenium trichloride. After the reaction mixture was stirred for 1 h at ambient temperature, TLC analysis (on silica gel plates eluted with 10% methanol in chloroform) showed that the starting material had been consumed in the reaction. After an additional 15 min of stirring, the reaction mixture was diluted with methylene chloride. The layers were separated and the aqueous layer was washed with methylene chloride. The combined methylene chloride layers were washed with brine, dried over anhydrous magnesium sulfate and concentrated in vacuo. The residue was purified by column chromatography on a 5×24 cm silica gel column eluted with 10% isopropyl alcohol in ethyl acetate. Fractions numbered 3–6 were combined and concentrated to give 2.37 g (64% yield) of 2,3-bis(benzoyloxymethyl)cyclopropyl carboxylic acid. DCI $NH_3$ MS, M/Z: 355 (M+H)+, 372 (M+$NH_4$)+ $^1$H NMR ($CDCl_{13}$) 2.01 (m, 2H), 2.19 (m, 1H), 4.31 (dt, 2H), 4.45 (m, 1H), 4.74 (m, 1H), 7.39 (m, 4H), 7.53 (m, 2H), 8.0 (m, 4H) ppm.

STEP F:
N-(Benzyloxycarbonyl)-[(1β,2α,3β)-2,3-bis(benzoyloxymethyl) cyclopropyl]amine 2,3-Bis(benzoyloxymethyl)cyclopropyl carboxylic acid (0.9 g, 2.54 mmol) from Step E, triethylamine (0.388 mL, 2.79 mmol) and diphenylphosphonylazide (DPPA) were added to 10 mL of toluene at ambient temperature. The reaction mixture was heated to 100° C. and stirred at 100° C. for 1 h. The reaction mixture was allowed to cool to ambient temperature and 0.289 mL (2.79 mmol) of benzyl alcohol was added. The reaction mixture was then heated to 80° C. and stirred at 80° C. for approximately 16 h. The reaction mixture was diluted with ethyl acetate, washed with 1 N hydrochloric acid solution and brine and concentrated in vacuo. The residue was purified by a series of column chromatographic separations on a silica gel column eluted with 50% ethyl acetate in hexane. The fractions containing pure N-(benzyloxycarbonyl) 2,3-bis(benzoyloxymethyl) cyclopropylamine were combined and concentrated in vacuo to give 315 mg (40% yield) of the title compound. DCI NH$_3$ MS, M/Z: 460 (M+H)$^+$, 477 (M+NH$_4$)$^+$. The 300 MHz $^1$H NMR spectrum is consistent with the proposed structure.

STEP G:
N-(Benzyloxycarbonyl)-(1β,2α,3β)-2,3-bis(hydroxymethyl) cyclporopyl]amine 7 N-(Benzyloxycarbonyl)-2,3-bis(benzoyloxymethyl) cyclopropylamine (0.22 g, 479 mmol) from Step F was dissolved in 5 mL of methanol. Sodium methoxide (52 mg, 95.9 mmol) was added to this solution and the reaction mixture was stirred at ambient temperature for 0.5 h. TLC analysis (on silica gel plates eluted with 10% methanol in chloroform) indicated that the starting material had been consumed in the reaction. The reaction mixture was concentrated in vacuo and the residue dissolved in water. The aqueous solution was acidified with Amberlite® IR-120(plus) acidic ion exchange resin. The resin was removed by filtration and the filtrate concentrated in vacuo. The residue was purified by column chromatography on a 2×20 cm silica gel column eluted with 5% methanol in methylene chloride. Fractions numbered 9 -14 were combined and concentrated in vacuo to give 51 mg (33.3% yield) of N-benzyloxycarbonyl 2,3-bis(hydroxymethyl) cyclopropylamine. DCI NH$_3$ MS, M/Z: 252 (M+H)$^+$, 269 (M+NH$_4$)$^+$. $^1$H NMR (CDCl$_3$) 1.10 (m, 1H, 1.40 (m, 1H), 1.59 (s, O-H), 2.60 (dd, 1H), 2.75 (N-H), 3.31 (ddd, 2H), 3.77 (dd, 1H), 4.00 (dd, 1H), 5.12 (s, 2H), 7.32 (m, 5H) ppm.

STEP H: (1β,2α,3β)
2,3-Bis(hydroxymethyl)cyclopropyllamine

N-(Benzyloxycarbonyl)-2,3-bis(hydroxymethyl) cyclopropylamine. (50 mg, 0.2 mmol) from Step G was dissolved in ethyl acetate and deprotected by hydrogenolysis using 10% palladium on carbon as a catalyst. The catalyst was removed by filtration and the filtrate concentrated under reduced pressure to give 19.9 g (85% yield) of 2,3-Bis(hydroxymethyl)cyclopropylamine. DCI NH$_3$ MS, M/Z: 118 (M+H)$^+$.

STEP I: 9-(1'β,
2'α,3'β)-2',3'-Bis(hydroxymethyl)cyclopropyl]adenine

The product of Step H, 2,3-Bis(hydroxymethyl)cyclopropylamine, is converted to 9-[2',3'-bis(hydroxymethyl)cyclopropyl]adenine by the procedures described in Example 4, Steps A through C for 9-[2-(1',2'-dihydroxyethyl)cyclopropyl]adenine.

EXAMPLE 7

9-(1', 2'α,
3'β)-2',3'-Bis(hydroxymethyl)cyclclopropyl]guanine

STEP A: (1α,262
)-3-Methylene-1,2-bis(tert-butyldimethylsilyloxymethyl)cyclopropane To a solution of 9.5 gm of the product of Example 6 (Step B) in 200 ml of CH$_2$Cl$_2$ was added sequentially 20 gm of imidazole and 26.3 gm of tert-butyldimethylsilyl chloride. The solution was stirred at RT for 2 hrs. The solid formed was filtered and washed with 100 ml of CH$_2$Cl$_2$. The combined CH$_2$Cl$_2$ solution was concentrated to an oil, which was chromatographed on silica gel (5% Et$_2$O/Hex) to give 26.5 gm of compound the desired product.

Mass spectrum: M$^+$=342

STEP B: (1α,2β,3α)-3-Hydroxymethyl-1,2-bis(tert butyldimethylsilyloxymethyl cyclopropane To a solution of 26.25 gm of the product of Example 7 (Step A) in 100 ml of dry THF, at 0° C. was added 168 ml of 0.5M solution of 9-BBN in THF. The solution was stirred at 0° C. for 0.5 hr and at RT for 2 hrs. The solution was cooled to 0° C. and carefully quenched with dropwise addition of water. To the solution at 0° C. was then added 27.8 ml of 3 M sodium hydroxide, followed by the addition of 26.25 ml of 30% hydrogen peroxide carefully. The resulting mixture was then stirred at RT for 40 min and concentrated on the rotavap. The residue was taken up in ether (200 ml) and washed with brine and extracted with ether (2×200 ml). The combined ether solution was dried and concentrated. The residual oil was purified by silica gel column chromatography (10% EtOAc/hexane) to give 25.6 gm of the desired product.

Mass spectrum: M$^+$=360

STEP C:
(1α,2β,3α)-2,3-bis(tert-butyldimethylsilyloxymethyl)-cyclopropane carboxaldehyde To 35 ml of dry CH$_2$Cl$_2$ cooled to −78° C. was added 3.12 ml of dry DMSO, followed by addition of 1.64 ml of oxalyl chloride. After 10 min, a solution of 5.0 gm of the product of Example 7 (Step B) in 70 ml of CH$_2$Cl$_2$ was added. The resulting reaction mixture was stirred for 30 min at −78° C. and 9.52 ml of triethylamine was added. The solution was stirred at −78° C. for 10 min and then at 0° C. for 20 min. The CH$_2$Cl$_2$ solution was washed with water
and the aqueous phase extracted with CH$_2$Cl$_2$ (100 m×2). The combined CH$_2$Cl$_2$ solution was dried with anhydrous sodium sulfate and filtered, concentrated on rotavap to give an oily residue which was purified by silica gel column chromatography (10% EtOAc/hexane) to give 4.2 gm of the desired product as a colorless oil.

$^1$H NMR (CDCl$_3$): δ0.01 (s, 12H), 0.83 (s, 18H), 1.72–1.80 (m, 1H), 1.90–1.95 (m, 2H), 3.63 (d, 2H), 3.65 (dd, 1H, J=7.5, 11.4 Hz), 3.94 (dd, 1H, J=5.1, 11.4 Hz), 9.43 (d, 1H, J=4.5 Hz).

STEP D: (1α,2β,3α)-2,3-bis
(tert-butyldimethylsilyloxymethyl)cyclopropane carboxylic acid To a solution of 4.2 gm of the product of Example 7 (Step C) in 63 ml of tert-butanol at RT was added 42 ml of 5% sodium dihydrogen phosphate. To the vigorously stirred reaction mixture was added 63 ml of 1 M KMnO$_4$ solution in portions. After 30 min, the excess KMnO$_4$ was quenched by addition of saturated sodium sulfite solution. The reaction mixture was extracted with ether (200 ml×3) and washed with brine and dried. The filtered ether solution was concentrated to a viscous oil and dried on vacuum pump for 3 hr to give 4.2 gm of the desired product as a colorless gummy solid which was used without purification.

Mass spectrum: M$^+$=374

STEP E:
N-(Benzyloxycarbonyl)-[(1β,2α,3β)-2,3-bis(tertbutyldimethylsilyloxymethyl)cyclopropyl]amine To a solution of 4.2 gm of the product of Example 7 (Step D) in 70 ml of benzene was added 5.7 ml of benzyl alcohol, 2.76 ml of diphenylphosphoryl azide, and 1.94 ml of triethylamine. The reaction mixture was heated at reflux for 20 hrs. The cooled reaction mixture was washed with 100 ml of water and extracted with ethyl acetate (100 ml×3) and the combined organic phase was washed with brine and dried, filtered, and concentrated to a residual oil which was purified by silica gel column chromatography (5% EtOAc/hexane) to provide 2.45 gm of the desired product.

Mass spectrum=M+ =479

STEP F: (1β,2α,3β)-2,3-bis(tert-butyldimethylsilyloxymethyl)cyclopropylamine To 200 mg of 10% Pd/C under $N_2$ was added 10 ml of methanol. To this suspension was added a solution of 2.4 gm of the product of Example 7 (Step E) in 20 ml of methanol. The reaction mixture was stirred vigorously under an atmosphere of $H_2$ (balloon pressure). After 0.5 hr, the catalyst was filtered and washed with 100 ml of methanol. The methanol solution was concentrated on the rotavap to provide 1.7 gm of the desired product which was used without further purification.

Mass spectrum: M+ =345

STEP G: 162-((2'-Amino-5'-nitro-6'-chloropyrimidin-4'-yl)amino)-(2α,3β)-2,3-bis(tert-butyldimethylsilyloxymethyl)cyclopropane To a solution of 1.7 gm of the product of Example 7 (Step F) in 20 ml of dimethylformamide was added 0.74 ml of triethylamine and 1.32 gm of 2-amino-4,6-dichloro-5-nitro pyrimidine. The solution was stirred at RT for 3 hrs. The DMF was removed under vacuum and the residual mixture was taken up in 100 ml of ethyl acetate and washed with brine and dried. The filtered solution was concentrated on the rotavap. The crude product was purified by silica gel column chromatography (20% EtOAc/hexane) to provide 1.0 gm of the desired product as a yellowish solid.

Mass spectrum: (M+H)+ =518

STEP H:
1β-(2',5'-diamino-6'-chloropyrimidin-4'-yl)amino)-(2α,3β)-2,3-bis(tert-butyldimethylsilyloxymethyl)cyclopropane To a suspension of ~500 mg of Raney nickel in 20 ml of absolute ethanol was added 500 mg of the product of Example 7 (Step G). The suspension was stirred vigorously under a hydrogen atmosphere for 0.5 hr and the catalyst was filtered off and washed with excess ethanol. The combined ethanol solution was concentrated on the rotavap. The residual solid was purified by silica gel column chromatography (30% EtOAc/hexane) to give 150 mg of the desired product as a pale yellow solid.

Mass spectrum: (M+H)+ =488

STEP I:
1β-(2'-Carbonylamino-6'-chloro-9'H-purin-9'-yl)-(2α,3β)-2,3-bis(tert-butyldimethylsilyloxymethyl)cyclopropane A solution of 150 mg of the product of Example 7 (Step H) in 18 ml of diethoxymethyl acetate was heated at reflux for 20 hrs. The solution was cooled to RT and concentrated under vacuum. The residue was chromatographed on silica gel (20% EtOAc/hexane) to provide 85 mg of the desired product as a white solid.

$^1$H NMR (DMSO-$d_6$): δ −0.2 (s, 6H), 0.1 (s, 6H), 0.66 (s, 9H), 0.88 (s, 9H), 1.60 (m, 1H), 2.08 (m, 1H), 3.37 (dd, 1H, J=7.5, 11.4 Hz), 3.60 (dd, 1H, J=3.5, 7.5 Hz), 3.77 (m, 2H), 3.96 (dd, 1H, J=4.5, 11.4 Hz).

STEP J:
9-((1'β,2'α,3'β)-2',3'-bis(tert-butyldimethylsilyloxymethyl)cyclopropyl)guanine To a solution of 35 mg of the product of Example 7 (Step I) in 3 ml of methanol was added 150 μl of mercaptoethanol, 80 mg of sodium methoxide, and 15 μl of water. The solution was heated to reflux for 1.5 hr. Forty mg of sodium methoxide was then added and the reaction mixture refluxed for an extra hour. The solution was cooled to 0° C. and acidified with 1 equivalent of acetic acid, concentrated on the rotavap, and the crude product was purified by silica gel column chromatography (5% MeOH/$CH_2Cl_2$) to provide 16 mg of the desired product.

$^1$H NMR (DMSO-$d_6$): δ−0.16 (s, 3H), −0.15 (s, 3H), 0.07 (s, 1H), 0.08 (s, 1H), 0.74 (s, 9H), 0.88 (s, 9H), 1.42 (m, 1H), 1.92 (m, 1H), 3.27 (m, 1H), 3.40 (m, 1H), 3.50 (m, 1H), 3.70 (m, 1H), 3.86 (m, 1H), 6.41 (br s, 2H), 7.60 (s, 1H), 10.51 (br s, 1H).

STEP K: 9-[(1'β,2'α,3'β)−2',3'-Bis(hydroxymethyl)]cyclopropyl guanine

To a solution of 39 mg of the product of Example 7 (Step J) in 4 ml of methanol was added 40 82 L of trimethylsilyl chloride. The solution was stirred at RT for 2 hr and concentrated on the rotavap. The residue was re-dissolved in 4 ml of methanol and a few drops of $NH_4OH$ solution was added. The solution was again concentrated on the rotavap and dried on the vacuum pump to give a white solid which was purified by C-18 column eluting first with water and then a gradient of 5-20% methanol in water to provide 18.5 mg of the desired product as a white solid.

Mass spectrum: (M+H)+ =252

$^1$H NMR (DMSO-$d_6$): δ1.42 (m, 1H), 1.65 (m, 1H), 3.07 (m, 1H), 3.18 (m, 1H), 3.32 (m, 1H), 3.50 (m, 1H), 3.60 (m, 1H), 4.50 (m, 1H), 4.67 (m, 1H), 6.50 (br s, 1H), 7.62 (s, 1H), 10.58 (br s, 1H).

EXAMPLE 8
1-(2'-(2''-Hydroxyethyl)cyclopropyl)uracil

STEP A: 2-(2'-((1'',1''-dimethylethyl)dimethylsilyl)-oxyethyl) cyclopropylamine To a stirred solution of 856 mg (8.55 mmol) of 2-(2'-hydroxy)ethylcyclopropylamine, from Step E of Example 1, in 50 mL of pyridine is added 2.58 g (17.1 mmol) of t-butyldimethylsilyl chloride. After 24 h, the reaction mixture is concentrated under reduced pressure and the residue is dissolved in a mixture of 100 mL of water and 100 mL of diethyl ether. The phases are separated and the organic phase is dried over anhydrous magnesium sulfate, filtered and concentrated under reduced pressure to afford the title compound.

STEP B:
N-(2'-(2''-(((1''',1'''-dimethylethyl)dimethylsilyl)oxy)ethyl) cyclopropyl)urea Triethylamine (TEA, 0.74 mL, 5.30 mmol) and 0.84 mL (5.34 mmol) of trimethylsilylisocyanate (85%, remainder hexamethyldisiloxane) are added to a stirred solution of 568 mg (2.64 mmol) of 2-(2'-(((1'',1''-dimethylethyl)dimethylsilyl) oxyethyl)cyclopropylamine, the product of Step A, in 50 mL of dry THF. After 16 h at reflux temperature, 0.42 mL (2.67 mmol) of trimethylsilylisocyanate and 0.37 mL (2.65 mmol) of TEA are added. After a total of 40 h at reflux temperature, 0.84 mL (5.34 mmol) of trimethylsilylisocyanate and 0.74 mL (5.30 mmol) Of TEA are added. After a total of 80 h at reflux, the cooled reaction mixture is concentrated under reduced pressure. Purification by column chromatography on silica gel eluted with 5% methanol in methylene chloride to 50% methanol in methylene chloride affords the title compound.

STEP C: 1-(2'-(2''-Hydroxyethyl)cyclopropyl)uracil (E)-3-Ethoxyacryloyl chloride (0.2 mL (1.5 mmol) is added to a stirred solution of 256 mg (0.996 mmol) of N-(2'-(2''-(((1''',1'''-dimethylethyl)dimethylsilyl)oxy)ethyl)cyclopropyl)urea, the product of Step B, in 15 mL of pyridine. After stirring for 5 h at ambient temperature, the reaction mixture is concentrated under reduced pressure. Purification of the residue by column chromatography on silica gel with a solvent gradient from 100% hexane to 20% acetone in hexane affords N-(N'-(2'-(2''-(((1''',1'''-dimethylethyl)dimethylsilyl) oxy)ethyl)cyclopropyl)carbamoyl)-3-ethoxypropenamide. Without further purification, 273 mg of this propenamide is dissolved in 16.3 mL of 2M aqueous sulfuric acid solution and heated to reflux temperature. After 1.5 h, the solution is allowed to cool, the pH of the solution adjusted to 6 with solid sodium bicarbonate, the solution saturated with sodium chloride and then continuously extracted with ethyl acetate for three days. The organic extracts are dried over anhydrous magnesium sulfate and concentrated under reduced pressure. Purification of the residue by column chromatography on silica gel eluted with a gradient of from 10% to 50% methanol in methylene chloride affords the title compound.

EXAMPLE 9
1-(2'-(1'',2''-Dihydroxyethyl)cyclopropyl)uracil

STEP A:
2-(1',2'-Bis(((1'',1''-dimethylmethyl)dimethylsilyl)oxy)ethyl) cyclopropylamine To a stirred solution of 992 mg (8.55 mmol) of 2-(1',2'-dihydroxyethyl)cyclopropylamine, from Step B of Example 3, in 50 mL of pyridine is added 2.58 g (17.1 mmol) of t-butyldimethylsilyl chloride. After 24 h, the reaction mixture is concentrated under reduced pressure and the residue is dissolved in a mixture of 100 mL of water and 100 mL of diethyl ether. The phases are separated and the organic phase is dried over anhydrous magnesium sulfate, filtered and concentrated under reduced pressure to afford the title compound.

STEP B:
N-(2'-(1'',2''-Bis(((1''',1'''-dimethylethyl)dimethylsilyl)oxy)ethyl)cyclopropyl)urea Triethylamine (TEA, 0.74 mL, 5.30 mmol) and 0.84 mL (5.34 mmol) of trimethylsilylisocyanate (85%, remainder hexamethyldisiloxane) are added to a stirred solution of 0.91 g (2.64 mmol) of 2-(1',2'-Bis((1'',1''-dimethylethyl)dimethylsilyl)oxyethyl) cyclopropylamine, the product of Step A, in 50 mL of dry THF. After 16 h at reflux temperature, 0.42 mL (2.67 mmol) of trimethylsilylisocyanate and 0.37 mL (2.65 mmol) of TEA are added. After a total of 40 h at reflux temperature, 0.84 mL (5.34 mmol) of trimethylsilylisocyanate and 0.74 mL (5.30 mmol) of TEA are added. After a total of 80 h at reflux, the cooled reaction mixture is concentrated under reduced pressure. Purification by column chromatography on silica gel eluted with 5% methanol in methylene chloride to 15% methanol in methylene chloride affords the title compound.

STEP C:
1-(2'-(1'',2''-Dihydroxy)ethylcyclopropyl)uracil (E)-3-Ethoxyacryloyl chloride (0.2 mL (1.5 mmol) is added to a stirred solution of 385 mg (0.996 mmol) of N-(2'-(1'',2''-Bis(((1''',1'''-dimethylethyl)dimethylsilyl)oxy)ethyl)cyclopropyl)urea, the product of Step B, in 15 mL of pyridine. After stirring for 5 h at ambient temperature, the reaction mixture is concentrated under reduced pressure. Purification of the residue by column chromatography on silica gel with a solvent gradient from 100% hexane to 20% acetone in hexane affords N-(N'-(2'-(1'',2''-Bis((1''',1'''dimethylethyl) dimethylsilyl)oxy)ethyl)cyclopropyl) carbamoyl)-3-ethoxypropenamide. Without further purification, 273 mg of this propenamide is dissolved in 16.3 mL of 2 M aqueous sulfuric acid solution and heated to reflux temperature. After 1.5 h, the solution is allowed to cool, the pH of the solution adjusted to 6 with solid sodium bicarbonate, the solution saturated with sodium chloride and then continuously extracted with ethyl acetate for three days. The organic extracts are dried over anhydrous magnesium sulfate and concentrated under reduced pressure. Purification of the residue by column chromatography on silica gel eluted with a gradient of from 10% to 20% methanol in methylene chloride affords the title compound.

EXAMPLE 10
1-(2'-(1'',2''-Diacetoxyethyl)cyclopropyl)uracil

To a stirred solution of 165 mg (0.78 mmol) of the product of Step C of Example 9 in 10 mL of acetonitrile is added 0.287 mL (2.06 mmol) of triethylamine (TEA), 7 mg (0.0585 mmol) of 4-dimethylaminopyridine (DMAP) 0.177 mL (1.87 mmol) of acetic anhydride. After 3 h at ambient temperature, the clear solution is treated with 1 mL of methanol, concentrated under reduced pressure and purified by column chromatography on silica gel to afford the title compound.

EXAMPLE 11

1-(1'β,2'α, 3'β)-(2',3'-Bis(hydroxymethyl)-cyclopropyl)]uracil

STEP A: [(1β, 2α,3β-2,3-Bis(((1',1'-dimethylethyl)dimethylsilyl)oxymethyl) cyclopropylamine To a stirred solution of 1.0 g (8.55 mmol) of 2,3-bis(-hydroxymethyl)cyclopropylamine in 50 mL of pyridine is added 2.58 g (17.1 mmol) of t-butyldimethylsilyl chloride. After 24 h, the reaction mixture is concentrated under reduced pressure and the residue is dissolved in a mixture of 100 mL of water and 100 mL of diethyl ether. The phases are separated and the organic phase is dried over anhydrous magnesium sulfate, filtered and concentrated under reduced pressure to afford the title compound.

STEP B: N-((1'β,2'α,3'β)-(2',3'-Bis(1",1"-dimethylethyl)dimethylsilyl) oxymethyl)cyclopropyl)urea Triethylamine (TEA, 0.74 mL, 5.30 mmol) and 0.84 mL (5.34 mmol) of trimethylsilylisocyanate (85%, remainder hexamethyldisiloxane) are added to a stirred solution of 0.91 g (2.64 mmol) of 2,3-Bis(((1',1'dimethylethyl)dimethylsilyl)oxymethyl) cyclopropylamine, the product of Step A, in 50 mL of dry THF. After 16 h at reflux temperature, 0.42 l mL (2.67 mmol) of trimethylsilylisocyanate and 0.37 mL (2.65 mmol) of TEA are added. After a total of 40 h at reflux temperature, 0.84 mL (5.34 mmol) of trimethylsilylisocyanate and 0.74 mL (5.30 mmol) of TEA are added. After a total of 80 h at reflux, the cooled reaction mixture is concentrated under reduced pressure. Purification by column chromatography on silica gel eluted with 5% methanol in methylene chloride to 50% methanol in methylene chloride affords the title compound.

STEP C: 1-[(1'β,2'α,3'β)-(2',340-Bis(hydroxymethyl)-cyclopropyl)]uracil (E)-3-Ethoxyacryloyl chloride (0.2 mL (1.5 mmol) is added to a stirred solution of 372 mg (0.996 mmol) of N-((2',3'-Bis((1",1"-dimethylethyl)dimethylsilyl)oxymethyl)cyclopropyl)urea, the product of Step A, in 15 mL of pyridine. After stirring for 5 h at ambient temperature, the reaction mixture is concentrated under reduced pressure. Purification of the residue by column chromatography on silica gel with a solvent gradient from 100% hexane to 20% acetone in hexane affords N,N'-((2',3'Bis((1",1"-dimethylethyl)dimethylsilyl)oxymethyl)cyclopropyl)carbamoy l)-3-ethoxypropenamide. Without further purification, 273 mg of this propenamide is dissolved in 16.3 mL of 2 M aqueous sulfuric acid solution and heated to reflux temperature. After 1.5 h, the solution is allowed to cool, the pH of the solution adjusted to 6 with solid sodium bicarbonte, the solution saturated with sodium chloride and then continuously extrated with ethyl acetate for three days. The organic extracts are dried over anhydrous magnesium sulfate and concentrated under reduced pressure. Purification of the residue by column chromatography on silica gel eluted with a gradient of from 10% to 20% methanol in methylene chloride affords the title compound.

EXAMPLE 12

1-(2'-(2"-Hydroxyethyl)cyclopropyl)cytosine

To 79 mg (0.42 mmol) of 1-(2'-(2"-hydroxyethyl)cyclopropyl) uracil, the product of Step B of Example 8, is added 0.44 mL (2.1 mmol) of hexamethyldisilazane and 0.034 mL (0.82 mmol) of formamide and the resultant mixture is heated with stirring in a sealed tube at 140° C. After 85 h, 10 mL of methanol is added to the cooled reaction mixture, the tube resealed and heated to 65° C. After 3 h at 65° C., the cooled reaction mixture is concentrated under reduced pressure. The residue is dissolved in 10 mL of water and the resultant aqueous solution treated with 50 mg of Darco G-60 charcoal, filtered and concentrated under reduced pressure. Purification of the residue by column chromatography on silica gel eluted with a gradient of methanol in methylene chloride from 100% methylene chloride to 30% methanol affords the title compound.

EXAMPLE 13

1-(2'-(1",2"-Dihydroxyethyl)cyclopropyl)cytosine

To 85.8 mg (0.42 mmol) of 1-(2'-(1",2"-dihydroxyethyl) cyclopropyl)uracil, the product of Step B of Example 9, is added 0.44 mL (2.1 mmol) of hexamethyldisilazane and 0.034 mL (0.82 mmol) of formamide and the resultant mixture is heated with stirring in a sealed tube at 140° C. After 85 h, 10 mL of methanol is added to the cooled reaction mixture, the tube resealed and heated to 65° C. After 3 h at 65° C., the cooled reaction mixture is concentrated under reduced pressure. The residue is dissolved in 10 mL of water and the resultant aqueous solution treated with 50 mg of Darco G-60 charcoal, filtered and concentrated under reduced pressure. Purification of the residue by column chromatography on silica gel eluted with a gradient of methanol in methylene chloride from 100% methylene chloride to 30% methanol affords the title compound.

EXAMPLE 14

1-[(1'β,2'α,3'β)-(2',3-Bis(hydroxymethyl)cyclopropyl)-]cytosine

To 89 mg (0.42 mmol) of 1-(2',3'-Bis(hydroxymethyl)cyclopropyl) uracil, the product of Step B of Example 11, is added 0.44 mL (2.1 mmol) of hexamethyldisilazane and 0.034 mL (0.82 mmol) of formamide and the resultant mixture is heated with stirring in a sealed tube at 140° C. After 85 h, 10 mL of methanol is added to the cooled reaction mixture, the tube resealed and heated to 65° C. After 3 h at 65° C., the cooled reaction mixture is concentrated under reduced pressure. The residue is dissolved in 10 mL of water and the resultant aqueous solution treated with 50 mg of Darco G-60 charcoal, filtered and concentrated under reduced pressure. Purification of the residue by column chromatography on silica gel eluted with a gradient of methanol in methylene chloride from 100% methylene chloride to 30% methanol affords the title compound.

EXAMPLE 15

1-(2'-(2"-Hydroxyethyl)cyclopropyl)thymine

3-Methoxymethacrylic acid chloride (2.68 g) and 25 mL of benzene are combined in a round bottom flask. To this mixture is added 6.4 g of silver cyanate and the resultant mixture heated to reflux temperature. After 40 min at reflux temperature the mixture is cooled to −15°

C. In a separate round bottom flask, 1.0 g of the product of Step A of Example 8, 30 mL of dimethyl formamide (DMF) and 10 mL of diethyl ether are combined and this second mixture cooled to −15° C. The acylisocyanate mixture is added to the amine and the resultant solution stirred at −15° C. for 2 h. and allowed to stand in the refrigerator overnight. The reaction mixture is concentrated and the crude material is purified by column chromatography. The material recovered from the column and 5 mL of 2N aqueous sulfuric acid solution are combined in a round bottom flask and this reaction mixture heated at reflux temperature for 2 h. The mixture is adjusted to pH 7 with aqueous barium hydroxide, filtered and the filtrate concentrated. The residue is purified by column chromatography to afford the title compound.

EXAMPLE 16

1-(2'-(1'',2''-Dihydroxyethyl)cyclopropyl)thymine

3-Methoxymethacrylic acid chloride (2.68 g) and 25 mL of benzene are combined in a round bottom flask. To this mixture is added 6.4 g of silver cyanate and the resultant mixture heated to reflux temperature. After 40 min at reflux temperature the mixture is cooled to −15° C. In a separate round bottom flask, 1.0 g of the product of Step A of Example 9, 30 mL of dimethyl formamide (DMF) and 10 mL of diethyl ether are combined and this second mixture cooled to −15° C. The acylisocyanate mixture is added to the amine and the resultant solution stirred at −15° C. for 2 h. and allowed to stand in the refrigerator overnight. The reaction mixture is concentrated and the crude material is purified by column chromatography. The material recovered from the column and 5 mL of 2N aqueous sulfuric acid solution are combined in a round bottom flask and this reaction mixture heated at reflux temperature for 2 h. The mixture is adjusted to pH 7 with aqueous barium hydroxide, filtered and the filtrate concentrated. The residue is purified by column chromatography to afford the title compound.

EXAMPLE 17

1-(2'-(1'',2''-Diacetoxyethyl)cyclopropyl)thymine

To a stirred solution of 176 mg (0.78 mmol) of the product of Example 16 in 10 mL of acetonitrile is added 0.287 mL (2.06 mmol) of triethylamine (TEA), 7 mg (0.0585 mmol) of 4-dimethylaminopyridine (DMAP) 0.177 mL (1.87 mmol) of acetic anhydride. After 3 h at ambient temperature, the clear solution is treated with 1 mL of methanol and concentrated under reduced pressure. The residue is purified by column chromatography on silica gel to afford the title compound.

EXAMPLE 18

1-(1'β, 2'α,3'β)-2',3'-Bis(hydroxymethyl)cyclopropyl]thymine

3-Methoxymethacrylic acid chloride (2.68 g) and 25 mL of benzene are combined in a round bottom flask. To this mixture is added 6.4 g of silver cyanate and the resultant mixture heated to reflux temperature. After 40 min at reflux temperature the mixture is cooled to −15° C. In a separate round bottom flask, the 1.0 g of product of Step H of Example 7 (2,3-bis(hydroxymethyl) cyclopropylamine), 30 mL of dimethyl formamide (DMF) and 10 mL of diethyl ether are combined and this second mixture cooled to −15° C. The acylisocyanate mixture is added to the amine and the resultant solution stirred at −15° C. for 2 h. and allowed to stand in the refrigerator overnight. The reaction mixture is concentrated and the crude material is purified by column chromatography. The material recovered from the column and 5 mL of 2N aqueous sulfuric acid solution are combined in a round bottom flask and this reaction mixture heated at reflux temperature for 2 h. The mixture is adjusted to pH 7 with aqueous barium hydroxide, filtered and the filtrate concentrated. The residue is purified by column chromatography to afford the title compound.

Antiviral Activity

The antiviral activity of the compounds of the invention can be determined by the following methods.

A. Evaluation of Compounds for In Vitro Activity Against Herpes Simplex Virus Types 1 and Types 2 and Human Influenza Virus Type A The challenge viruses were propagated and assayed in cells that were pregrown as monolayer cultures in plastic tissue culture flasks and 96-well plates, using cell culture media appropriate for the host cell cultures. The following viruses and host cell cultures were employed:

| Challenge Virus | Host Cell Type |
|---|---|
| Herpes simplex type 1 (HSV-1) strain E-377 | Continuous-passage African green monkey kidney (Vero) |
| Herpes simplex type 2 (HSV-2) strain MS | Continuous-passage African green monkey kidney (Vero) |
| Human influenza type A (IV-A) strain PR/8/34 (H1N1) | MDCK (Madin-Darby Canine Kidney) |

On the day of use, a weighed sample of each compound to be evaluated was dissolved and diluted in serial $10^{0.5}$ dilutions in the culture medium appropriate for each virus-host cell system.

CPE-Inhibition Assay Procedure

Mammalian cells were pregrown as monolayers in wells of COSTAR 96-well tissue culture plates using suitable cell culture media. Stock viruses were pretitered according to the method of Reed and Muench (Amer. J. Hyg. 27:493–497, 1938) and diluted in cell culture medium to yield 32 $CCID_{50}$ (cell culture infectious dose, 50%) units per 0.1 ml. Antiviral assays were designed to test seven concentrations of each compound, from cytotoxic to noncytotoxic levels, in triplicate against each of the challenge viruses in microtiter plate wells containing suitable cell monolayers. To each of the replicate cell cultures were added 0.1 ml of the test drug solution and 0.1 ml of virus suspension. Cell controls containing medium alone, virus controls containing medium and virus, and drug cytotoxicity controls containing medium and each drug concentration were run simultaneously with the test samples assayed in each experiment. The covered plates were incubated at 37° C. in a humidified atmosphere containing 5% $CO_2$ until maximum CPE (cytopathogenic effect) was observed in the untreated virus control cultures. The cell monolayers were examined microscopically for virus-induced CPE and for drug cytotoxicity.

Antiviral activity was determined by calculating the degree of inhibition of virus-induced CPE in drug-treated, virus-infected cell cultures by means of a virus rating (VR). The VR is a standard weighted measurement of antiviral activity taking into account both the degree of CPE inhibition and drug cytotoxicity, and is determined by a modification of the method of Ehrlich et al. (Ann. N.Y. Acad. Sci. 130 : 5-16, 1965) as described below. CPE was graded for each individual culture in each microtiter plate well according to the following scale:

4=100% of the cells affected by virus;
3=75% of the cells affected by virus;
2=50% of the cells affected by virus;
1=25% of the cells affected by virus;
0=No CPE; normal cell monolayer;

The VR was calculated as 0.1 of the sum of the numerical differences between the recorded CPE grade of each test well and that of the corresponding virus control in the culture plate. Numerical differences between the scores of test wells containing a drug concentration which was partially cytotoxic (p) and their corresponding virus controls were halved.

The minimum inhibitory drug concentration which reduced the cytopathogenic effect (CPE) by 50% ($MIC_{50}$) was calculated by using a regression analysis program for semilog curve fitting. A therapeutic index (TI) for each active compound for each susceptible virus was determined by dividing the minimum cytotoxic concentration of the test compound by the $MIC_{50}$. Test results are provided in Tables 1 and 2.

TABLE 1

Antiviral Activity of Compounds of Formula I Against Herpes Simplex

| | Challenge Virus | | | | | | |
|---|---|---|---|---|---|---|---|
| | Herpes Simplex | | | | Herpes Simplex | | |
| | Host Cell Type | | | | | | |
| Compound of | Type 1 (E-377) Vero | | | | Type 2 (MS) Vero | | |
| Example No. | VR[1] | ID50[2] | MTC[3] | TI[4] | VR | ID50 | MTC | TI |
| 3G | 1.8 | 101.0 | >320 | 3.2 | 1.3 | 159.0 | >320 | 2.0 |
| 2E | 3.7 | 31.6 | >320 | >10.4 | 2.3 | 77.7 | >320 | >4.1 |

[1] VR=Virus Rating: A measurement of selective antiviral activity which takes into account the degree of virus-induced cytopathogenic effects (CPE) and the degree of cytotoxicity produced by the test compound, determined by a modification of the method of Ehrlich et al. (Ann. N.Y. Acad. Sci. 130: 5-16, 1965). A VR |1.0 indicates definite (+) antiviral activity, a VR of 0.5-0.9 indicates marginal to moderate antiviral activity, and a VR<0.5 usually indicates no significant antiviral activity.

[2] ID50=The minimum drug concentration (ug/ml) that inhibited the CPE by 50%, calculated by using a regression analysis program for semilog curve fitting.

[3] MTC=The minimum drug concentration (ug/ml) causing any cytotoxicity.

[4] TI=Therapeutic Index, calculated by dividing the minimum cytotoxic drug concentration by the ID50.

The results indicate that the compounds are active against HSV.

TABLE 2

Antiviral Activity of Compounds of Formula I Against Human Influenza

| Challenge Virus: | Human Influenza Type A (IV-A) | | | |
|---|---|---|---|---|
| Host Cell Type: | MDCK | | | |
| Compound of Example No. | VR | ID50 | MTC | TI |
| 3G | 0.6 | | >320 | |

The results indicate that the compound is active against human influenza virus.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptonate, glycerophosphate, hemisulfate, heptonate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases.

The novel compounds of the present invention possess antiviral activity and are useful for treating or preventing virus related diseases. Compounds of the invention are effective against herpes viruses and influenza virus. Compounds of the invention are particularly effective against herpes viruses.

Total daily dose administered to a host in single or divided doses may be in amounts, for example, from 0.1 to 2000 mg/kg body weight daily and more usually 1.0 to 500 mg/kg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of ointments, creams or ophthalmically acceptable solutions, suspensions, emulsions, ointments and solid inserts. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

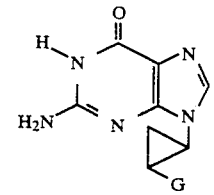

wherein G is —CH$_2$CH$_2$OH or —CH(OH)CH$_2$; or a pharmaceutically acceptable salt thereof.

2. 9-(2'-(2''-hydroxyethyl)cyclopropyl)guanine.

3. 9-(2'-(1'',2''-dihydroxyethyl)cyclopropyl)guanine.

4. A method of treating susceptible viral infections comprising administering to a human in need of such treatment an effective amount of a compound of claim 1.

5. A pharmaceutical composition comprising a pharmaceutical carrier and an effective amount of a compound of claim 1 for treating a susceptible viral infection.

* * * * *

UNITED STATES PATENT AND TRADEMARK OFFICE
CERTIFICATE OF CORRECTION

PATENT NO. : 4,988,703

DATED : January 29, 1991

INVENTOR(S) : DANIEL W. NORBECK; TERRY J. ROSEN

It is certified that error appears in the above-identified patent and that said Letters Patent is hereby corrected as shown below:

On title page, line 3 of item [75], delete "HING L. SHAM, Gurnee, Illinois".

On title page, Column 2, line 19, after "—$CO_2R_1$" delete --[--.

Column 42, line 34, replace "—CH(OH)$CH_2$" with -- -CH(OH)$CH_2$OH--.

Signed and Sealed this

Fourteenth Day of July, 1992

Attest:

DOUGLAS B. COMER

Attesting Officer

Acting Commissioner of Patents and Trademarks